(12) United States Patent  
Rigas

(10) Patent No.: US 12,414,710 B2
(45) Date of Patent: Sep. 16, 2025

(54) BREATH ANALYZER DEVICES AND BREATH TEST METHODS

(71) Applicant: Anastasia Rigas, Setauket, NY (US)

(72) Inventor: Anastasia Rigas, Setauket, NY (US)

( * ) Notice: Subject to any disclaimer, the term of this patent is extended or adjusted under 35 U.S.C. 154(b) by 1113 days.

(21) Appl. No.: 17/312,909

(22) PCT Filed: Dec. 10, 2019

(86) PCT No.: PCT/US2019/065556
§ 371 (c)(1),
(2) Date: Jun. 10, 2021

(87) PCT Pub. No.: WO2020/123565
PCT Pub. Date: Jun. 18, 2020

(65) Prior Publication Data
US 2022/0039690 A1     Feb. 10, 2022

Related U.S. Application Data

(60) Provisional application No. 62/777,759, filed on Dec. 10, 2018.

(51) Int. Cl.
*A61B 5/083*     (2006.01)
*A61B 5/00*     (2006.01)
*A61B 5/097*     (2006.01)

(52) U.S. Cl.
CPC ............ *A61B 5/0836* (2013.01); *A61B 5/097* (2013.01); *A61B 5/4222* (2013.01); *A61B 5/4244* (2013.01); *A61B 2562/0285* (2013.01)

(58) Field of Classification Search
None
See application file for complete search history.

(56) References Cited

U.S. PATENT DOCUMENTS

| | | |
|---|---|---|
| 3,852,036 A | 12/1974 | Burroughs et al. |
| 3,953,173 A | 4/1976 | Obayashi et al. |
| 4,007,063 A | 2/1977 | Yasuda et al. |
| 4,030,340 A | 6/1977 | Chang |
| 4,140,106 A | 2/1979 | Kirmaier |

(Continued)

FOREIGN PATENT DOCUMENTS

| | | |
|---|---|---|
| CN | 109164140 A | 1/2019 |
| DE | 29902593 U1 | 7/1999 |

(Continued)

OTHER PUBLICATIONS

Penner, J.L. et al., Serotyping of *Campylobacter jejuni* and *Campylobacter coli* on the Basis of Thermostable Antigens. Eur J Clin Microbial. (1983) 2:378-383.

(Continued)

*Primary Examiner* — Aurelie H Tu
(74) *Attorney, Agent, or Firm* — Nexus Law PLLC

(57) ABSTRACT

The present invention provides an improved breath analyzer and breath test method to determine the presence of disease in humans, including but not limited to, the bacterium *H. pylori* in a subjects digestive tract. In certain embodiments, the present invention provides a universal breath testing platform and methods of testing for diseases of the gastrointestinal tract, the liver, the kidneys, and the lungs, along with testing for cancer, infections, and metabolic diseases.

8 Claims, 22 Drawing Sheets

(56) References Cited

U.S. PATENT DOCUMENTS

| | | | |
|---|---|---|---|
| 4,169,369 A | 10/1979 | Chang | |
| 4,346,583 A | 8/1982 | Hoogstraat | |
| 4,430,191 A | 2/1984 | Sone et al. | |
| 4,481,499 A | 11/1984 | Arima et al. | |
| 4,753,916 A | 6/1988 | Carcia et al. | |
| 4,823,803 A | 4/1989 | Nakamura | |
| 4,858,063 A | 8/1989 | Laue et al. | |
| 4,895,705 A | 1/1990 | Wrighton et al. | |
| 4,947,861 A | 8/1990 | Hamilton | |
| 5,037,525 A | 8/1991 | Badwal | |
| 5,055,441 A | 10/1991 | Mccarron et al. | |
| 5,069,220 A | 12/1991 | Casparie et al. | |
| 5,252,292 A | 10/1993 | Hirata et al. | |
| 5,331,287 A | 7/1994 | Yamagishi et al. | |
| 5,531,225 A | 7/1996 | Nawata et al. | |
| 5,546,004 A | 8/1996 | Schmelz | |
| 5,624,640 A | 4/1997 | Potthast et al. | |
| 5,783,154 A | 7/1998 | Althainz et al. | |
| 5,787,885 A | 8/1998 | Lemelson | |
| 5,811,662 A | 9/1998 | Williams et al. | |
| 5,858,186 A | 1/1999 | Glass | |
| 5,869,007 A | 2/1999 | Jang | |
| 5,969,231 A | 10/1999 | Qu et al. | |
| 5,993,625 A | 11/1999 | Inoue et al. | |
| 6,156,346 A | 12/2000 | Chen et al. | |
| 6,173,602 B1 | 1/2001 | Moseley | |
| 6,173,603 B1 | 1/2001 | Horn | |
| 6,186,958 B1 | 2/2001 | Katzman et al. | |
| 6,234,006 B1 | 5/2001 | Sunshine et al. | |
| 6,319,724 B1 | 11/2001 | Lewis et al. | |
| 6,411,905 B1 | 6/2002 | Guoliang et al. | |
| 6,467,333 B2 | 10/2002 | Lewis et al. | |
| 6,491,643 B2 | 12/2002 | Katzman et al. | |
| 6,606,566 B1 | 8/2003 | Sunshine | |
| 6,609,068 B2 | 8/2003 | Cranley et al. | |
| 6,620,109 B2 | 9/2003 | Hanson | |
| 6,660,231 B2 | 12/2003 | Moseley | |
| 6,703,241 B1 | 3/2004 | Sunshine et al. | |
| 6,723,056 B1 | 4/2004 | Alving et al. | |
| 6,730,212 B1 | 5/2004 | Yamagishi et al. | |
| 6,767,732 B2 | 7/2004 | Alocilja et al. | |
| 6,820,012 B2 | 11/2004 | Sunshine | |
| 6,839,636 B1 | 1/2005 | Sunshine et al. | |
| 6,841,391 B2 | 1/2005 | Lewis et al. | |
| 6,981,947 B2 | 1/2006 | Melker | |
| 7,014,612 B2 | 3/2006 | Hubbard et al. | |
| 7,017,389 B2 | 3/2006 | Gouma | |
| 7,101,340 B1 | 9/2006 | Braun | |
| 7,104,963 B2 | 9/2006 | Melker et al. | |
| 7,189,360 B1 | 3/2007 | Ho | |
| 7,220,387 B2 | 5/2007 | Flaherty et al. | |
| 7,338,454 B2 | 3/2008 | Butler et al. | |
| 7,364,551 B2 | 4/2008 | Allen et al. | |
| 7,522,040 B2 | 4/2009 | Passmore et al. | |
| 7,640,789 B2 | 1/2010 | Kim et al. | |
| 7,687,275 B2 | 3/2010 | Burdinski | |
| 7,704,214 B2 | 4/2010 | Abraham-Fuchs et al. | |
| 7,867,171 B2 | 1/2011 | Ben-Oren et al. | |
| 7,950,271 B2 | 5/2011 | Novak et al. | |
| 7,981,215 B2 | 7/2011 | Gouma et al. | |
| 8,263,002 B1 | 9/2012 | Chow et al. | |
| 8,343,484 B2 | 1/2013 | Farmer et al. | |
| 8,485,983 B2 | 7/2013 | Gouma et al. | |
| 9,289,155 B2 | 3/2016 | Rigas et al. | |
| 9,541,517 B2 | 1/2017 | Samuilov | |
| 9,643,186 B1 | 5/2017 | Ahmad et al. | |
| 2002/0011569 A1 | 1/2002 | Mori et al. | |
| 2002/0090667 A1 | 7/2002 | Ratcliffe et al. | |
| 2002/0159950 A1 | 10/2002 | Wagner | |
| 2003/0008407 A1 | 1/2003 | Fu | |
| 2003/0105407 A1 | 6/2003 | Pearce, Jr. et al. | |
| 2003/0175699 A1 | 9/2003 | Tachikawa et al. | |
| 2003/0208133 A1 | 11/2003 | Mault | |
| 2003/0217586 A1 | 11/2003 | Gouma | |
| 2004/0077093 A1* | 4/2004 | Pan | A61B 5/42 436/37 |
| 2004/0077965 A1 | 4/2004 | Hubbard et al. | |
| 2005/0100535 A1 | 5/2005 | Farmer et al. | |
| 2005/0129573 A1 | 6/2005 | Gabriel et al. | |
| 2005/0171449 A1 | 8/2005 | Suslick et al. | |
| 2005/0177056 A1* | 8/2005 | Giron | A61M 16/085 600/543 |
| 2006/0074335 A1 | 4/2006 | Ben-Oren et al. | |
| 2006/0147496 A1 | 7/2006 | Lin et al. | |
| 2006/0174385 A1 | 8/2006 | Gruber et al. | |
| 2006/0277974 A1 | 12/2006 | Gouma et al. | |
| 2007/0048180 A1 | 3/2007 | Gabriel et al. | |
| 2007/0048181 A1 | 3/2007 | Chang et al. | |
| 2007/0167691 A1 | 7/2007 | Causevic | |
| 2007/0209937 A1 | 9/2007 | Hoagland et al. | |
| 2007/0256477 A1 | 11/2007 | Moor | |
| 2007/0272901 A1 | 11/2007 | Gouma | |
| 2008/0053194 A1 | 3/2008 | Ahmad | |
| 2008/0077037 A1 | 3/2008 | Gouma et al. | |
| 2008/0093226 A1 | 4/2008 | Star et al. | |
| 2008/0317636 A1 | 12/2008 | Brahim et al. | |
| 2009/0031784 A1 | 2/2009 | Koda et al. | |
| 2009/0044597 A1* | 2/2009 | Kvasnik | A61B 5/097 73/23.3 |
| 2009/0054799 A1 | 2/2009 | Vrtis et al. | |
| 2009/0187111 A1 | 7/2009 | Reilly, Jr. et al. | |
| 2009/0266411 A1 | 10/2009 | Habib et al. | |
| 2009/0294303 A1 | 12/2009 | Fischer et al. | |
| 2010/0006434 A1 | 1/2010 | Virji et al. | |
| 2010/0012919 A1 | 1/2010 | Park et al. | |
| 2010/0089772 A1 | 4/2010 | Deshusses et al. | |
| 2010/0209507 A1 | 8/2010 | Lin et al. | |
| 2010/0212403 A1 | 8/2010 | Seal et al. | |
| 2010/0215738 A1 | 8/2010 | Ritter et al. | |
| 2011/0056846 A1 | 3/2011 | Neethirajan et al. | |
| 2011/0061446 A1 | 3/2011 | Gouma et al. | |
| 2011/0259083 A1 | 10/2011 | Lee et al. | |
| 2011/0300637 A1 | 12/2011 | Virji et al. | |
| 2012/0034646 A1 | 2/2012 | Rigas et al. | |
| 2012/0065534 A1 | 3/2012 | Rigas | |
| 2012/0186999 A1 | 7/2012 | Walton et al. | |
| 2012/0234076 A1 | 9/2012 | Rigas | |
| 2012/0237968 A1 | 9/2012 | Rigas | |
| 2013/0289368 A1 | 10/2013 | Covington et al. | |
| 2014/0221863 A1 | 8/2014 | Rigas | |
| 2014/0330153 A1 | 11/2014 | Gouma et al. | |
| 2015/0201865 A1 | 7/2015 | Forzani et al. | |
| 2015/0250407 A1 | 9/2015 | Rigas | |
| 2016/0097761 A1 | 4/2016 | Sano et al. | |
| 2016/0103082 A1 | 4/2016 | Kimura | |
| 2017/0105656 A1* | 4/2017 | Rigas | G01N 33/497 |
| 2017/0191953 A1 | 7/2017 | Rigas | |
| 2017/0321010 A1 | 11/2017 | Kinlen et al. | |
| 2019/0357807 A1 | 11/2019 | Jiang et al. | |

FOREIGN PATENT DOCUMENTS

| | | |
|---|---|---|
| JP | 2012202874 A | 10/2012 |
| KR | 101314303 B1 | 10/2013 |
| WO | 0193915 A1 | 12/2001 |
| WO | 0206822 A1 | 1/2002 |
| WO | 03041565 A2 | 5/2003 |
| WO | 2009039152 A1 | 3/2009 |
| WO | 2011004567 A1 | 1/2011 |
| WO | 2012125734 A2 | 9/2012 |
| WO | 2012125745 A2 | 9/2012 |
| WO | 2014056961 A1 | 4/2014 |
| WO | 2014063169 A1 | 4/2014 |
| WO | 2015179751 A1 | 11/2015 |
| WO | 2015179755 A1 | 11/2015 |

OTHER PUBLICATIONS

Corazza et al., "Fast Breath Hydrogen in Celiac Disease," Pub Med, Gastroenterology, vol. 93, No. 1, Jul. 1987, pp. 53-58.

(56) References Cited

OTHER PUBLICATIONS

Surveyor, Ivor et al., The 14C-urea breath-test for the detection of gastric Campylobacter pylori infection. Med J Aust (1989) 151:435-439.

Hu, Li Tai et al., Purification and N-terminal analysis of urease from *Helicobacter pylori*. Infect Immun (1990) 58:992-998.

Wang, Xiaodong et al., An integrated array of multiple thin-film metal oxide sensors for quantification of individual components in organic vapor mixtures, Sensors and Actuators B, (1993) 13-14, 458-461.

Murnick, D.E. et al., Laser-Based Analysis of Carbon Isotope Ratios. Science (1994) 263:945-947, retrieved from the Internet on Mar. 22, 2016 at <URL: http://science.sciencemag.org/content/263/5149/945.full-text.pdf+html>.

Cutler, Alan F. et al., Accuracy of invasive and noninvasive tests to diagnose *Helicobacter pylori* infection, Gastroenterology (1995) 109:136-141, American Gastroenterological Association.

Sberveglieri, G. et al., WO3 sputtered thin films for NOx monitoring, Sensors and Actuators B 26 (1995) pp. 89-92.

Slomianski, Arie et al., [13C]urea breath test to confirm eradication of *Helicobacter pylori*. Am J Gastroentero. (1995) 90:224-226.

Brandli, 0. et al., Lung function in healthy never smoking adults: reference values and lower limits of normal of a Swiss populatio. Thorax (1996) 51:277-283. Retrieved from the Internet on Mar. 19, 2016 at < http://thorax.bmj.com/>.

Cutler, Alan F., Testing for *Helicobacter pylori* in clinical practice. Symposium on *Helicobacter Pylori*, Am J Med (1996) 100:35S-41S, Supplement 5 [Discussion pp. 39S-41S].

Harris, Adam et al., Treating *Helicobacter pylori*—the best is yet to come? Gut (1996) 39:781-783, retrieved from the Internet on Mar. 19, 2016 at <URL: http://gut.bmj.com/>. Published by group.bmj.com.

Klein, Peter O. et al., Noninvasive detection of *Helicobacter pylori* infection in clinical practice: the 13C urea breath est. Am J Gastroentero. (1996) 91:690-694.

Mutschall, D., et al., Sputtered molybdenum oxide thin films for NH3 detection 1996 Sensor and Actuators B35-36, p. 320-324.

Dunn, B.E. et al., *Helicobacter pylori*. Clinical Microbiology Reviews (1997) pp. 720-741, vol. 10, Issue 4, retrieved from the Internet on Mar. 19, 2016 at <URL: http://cmr.asm.org/>.

Monteiro, Lurdes et al., Evaluation of performances of three DNA enzyme immunoassays for detection of *Helicobacter pylori* PCR products from biopsy specimens. J Clin Microbiol. (1997) 35:2931-2936.

Gouma, P.I. et al., Microstructural Characterization of Sensors based on Electronic Ceramic Materials, JOM, 50 (11), presented as JOM-e., Nov. 1998, 15 pages.

Humerfelt, S., et al., Forced expiratory volume in 1 second (FEV1) and forced vital capacity (FVC) variability in asymptomatic neversmoking men. Clin Physio. (1998) 18:387-396.

Chung, Yong-Keun et al., Gas sensing properties of WO3 thick film for NO2 gas dependent on process condition, Sensors and Actuators B: Chemical (1999) 60:49-56 <doi:10.1016/S0925-4005(99)00243-9>.

Dutta, Prabir, et al., Interaction of Carbon Monoxide with Anatase Surfaces at High Temperatures: Optimization of a Carbon Monoxide Sensor, J. Phys. Chem. B., 103, pp. 4412-4419, (1999).

Eslick, G.D. et al., Association of *Helicobacter pylori* infection with gastric carcinoma: a meta-analysis. Am J Gastroenterol (1999) 94:(9) 2373-2379.

Ferroni, A. et al., Nanosized thin films of tungsten-titanium mixed oxides as gas sensors, Sensors and Actuators B 58 (1999) pp. 289-294.

Gouma, P.I. et al., Structural Stability of Titania Thin Films, Nanostructured Materials (1999) 11(8), pp. 1231-1237.

Alcoscan Al2000 Alcohol Breath Analyzer, Craig Medical Distribution Inc., 3 pages, retrieved from Internet on 3/29/3026 at <URL: http://www.craigmedical.com/alcoscan_AL_2000.htm.

Gouma, Pelagia I. et al., Fabrication of Free-Standing Titania-Based Gas Sensors by the Oxidation of Metallic Titanium Foils. J. Am Ceramic. Soc., 83(4), pp. 1007-1009, 2000.

Imawan, C., et al., Gas-sensing characteristics of modified-MoO2 thin films using Ti-overlayers for NH3 gas sensors, Sensors and Actuators B. 64 (2000) pp. 193-197.

Xu, C.N. et al., Selective detection of NH over NO in combustion exhausts by using Au and MoO3 doubly promoted WO element. Sensors and Actuators B, (2000) 65, pp. 163-165.

Abdel-Saheb, Ibrahim, Memorandum: Review of Urea, as an Active and Inert Ingredient Environmental Protection Agency, (2001) Retrieved from Internet on Apr. 1, 2016 at <URL: http://web.archive.org/web/20040722194412/http://www.epa.gov/oppsrrd1/reregistration/urea/UreaEnviron.pdf> 14 pages.

Casellas et al., "Hydrogen Breath Test with D-Xylose for Celiac Disease Screening Is as Useful in the Elderly as In Other Age Groups," Digestive Deseases and Sciences, Oct. 2001, vol. 46, No. 10, pp. 2201-2205.

Eshun, J.K. et al., Comparison of immunohistochemistry and silver stain for the diagnosis of pediatric *Helicobacter pylori* infection in urease-negative gastric biopsies. Pediatr Dev Patho (2001) 4:82-88.

Guidi, V. et al., Nanosized Ti-doped MoO3 thin films for gas-sensing application. Sens and Act B, (2001) 77:555-560.

Imawan, C. et al., A new preparation method for sputtered MoO3 multilayers for the application in gas layers, Sensors and Actuators B. 78 (2001) pp. 119-125.

Kharitonov, Sergei A. et al., Exhaled markers of pulmonary disease. Am J Respir Crit Care Med (2001) 163:1693-1722.

Livage, Jacques et al., Encapsulation of biomolecules in silica gels. J. Phys.: Condens. Matter 13 (2001) pp. R673-R691, retrieved from the Internet on Mar. 20, 2016 at <URL: http://iopscience.iop.org/.

Marquis, Brent T. et al., A semiconducting metal oxide sensor array for the detection of NOx and NH3, Sensors and Actuators B 77 (2001) pp. 100-110.

Dai, Liming, et al., Sensors and sensor arrays based on conjugated polymers and carbon nanotubes; Pure App. Chem., vol. 74, No. 9, pp. 1753-1772, 2002.

Go, M.F. Review article: natural history and epidemiology of *Helicobacter pylori* infection. Aliment Pharmacol Ther 16 Suppl (2002) 1:3-15.

Kato, Seiichi et al., Diagnostic Accuracy of the 13C-Urea Breath Test for Childhood *Helicobacter pylori* Infection: A Multicenter Japanese Study The American J of Gastroenterology, (2002) 97(7):1668-1673.

Kearney, David J. et al., Breath Ammonia Measurement in *Helicobacter pylori* Infection, Dig Dis Sci (2002) 47:2523-2530.

Leong, R.W. et al., Review article: *Helicobacter* species and hepatobiliary diseases. Aliment Pharmacal Ther (2002) 16:1037-1045.

Phillips, Michael, Detection of Volatile Organic Compounds in Breath. In "Disease markers in exhaled breath" eds Marczin N. Kharitonov SA, Yacoub MH and Barnes PJ. Marcel Decker. (2002) pp. 219-231, New York.

Stejskal, J., Polyaniline. Preparation of a Conducting Polymer (IUPAC Technical Report). Pure Appl. Chem., (2002) vol. 74, No. 5, pp. 857-867, International Union of Pure and Applied Chemistry.

Gatta, L. et al., A rapid, low-dose, 13C-urea tablet for the detection of Helicobacter pylori infection before and after treatment. Aliment Pharmacal Ther (2003) 17:793-798.

Prasad, A.K. et al., Comparison of solgel and ion beam deposited MoO3 thin film gas sensors for selective ammonia detection. Sens Actuators B. (2003) 93:25-30.

Prasad, A.K., et al., Reactivity sputtered Mo03 films for ammonia sensing. Thin Solid Films (2003) 436:46-51.

Versalovic, James, *Helicobacter pylori*. Pathology and diagnostic strategies. Am J Clin Patho (2003) 119:403-412. Retrieved from the Internet on Mar. 22, 2016 at <URL: http://ajcp.oxfordjournals.org>.

Gisbert, J.P. et al., Review article: 13C-urea breath test in the diagnosis of *Helicobacter pylori* infection a critical review. Aliment Pharmacal Ther (2004) 20:1001-1017.

Gouma, P. et al., Novel Materials and Applications of Electronic Noses and Tongues; MRS. Bulletin, Oct. 2004, pp. 697-702.

(56) References Cited

OTHER PUBLICATIONS

Graham, D.Y., et al., Challenge model for *Helicobacter pylori* infection in human volunteers. Gut (2004) 53:1235-1243, retrieved the Internet on Mar. 19, 2016 at <URL: http://gut.bmj.com/>. Published by group.bmj.com.

Pardo, Matteo et al., Electronic Olfactory Systems Based on Metal Oxide Semiconductor Sensor Arrays. MRS Bulletin, Oct. 2004, pp. 703-708, Materials Research Society http://www.mrs.org/publications/.

Ryan, M.A. et al., PolymerCarbon Black Composite Sensors in an Electronic Nose for Air-Quality Monitoring; MRS Bulletin, Oct. 2004, pp. 714-719.

Suslick, Kenneth S., an Optoelectronic Nose: "Seeing" Smells by Means of Colorimetric Sensor Arrays; MRS Bulletin, Oct. 2004, pp. 720-725, Materials Research Society http://www.mrs.org/publications/.

Winquist, F. et al., Electronic Tongues. MRS Bulletin, Oct. 2004, pp. 726-731, Materials Research Society http://www.mrs.org/publications/.

Agha et al., "Evidence-based examination of the African enigma in relation to Helicobacter pylori infection," Scandinavian Journal of Gastroenterology (2005) 40:523-529, Taylor & Francis Group Ltd, United Kingdom.

Chen, Jyh-Cherng et al., Removal of carbon dioxide by a spray dryer, Chemosphere, (2005) 59:99-105, <doi: 10.1016/j.chemosphere.2004.09.076>.

Delaney, B., et al., Review article: *Helicobacter pylori* and gastroesophageal reflux disease. Aliment Pharmscol Ther (2005) 22 Suppl 1 :32-40.

Di Francesco, F., et al., Breath analysis: trends in techniques and clinical applications. Microchemical Journal (2005) 79:105-410.

Sadek et al., "A Room Temperature Polyaniline Nanofiber Hydrogen Gas Sensor," Sensor Technology Laboratory, RMIT University, 2005 IEEE, pp. 207-210.

Timmer, Bjorn et al., Ammonia sensors and their applicationsa review. Sensors and Actuators B, 2005, 107:666-677.

Vaira, Dino et al., Peptic ulcer and *Helicobacter pylori*: update on testing and treatment. Postgrad Med (2005) 117:17-22, 46. Retrieved from the Internet on Mar. 22, 2016 at <URL: http://dx.doi.org/10.3810/pgm.2005.06.1654> Taylor & Francis Ltd.

Gisbert, J.P. et al., Accuracy of *Helicobacter pylori* Diagnostic Tests in Patients with Bleeding Peptic Ulcer: A Systematic Review and Meta-analysis. Am J Gastroenterol (2006) 101:848-863.

Gouma, P.I. et al., Selective nanoprobes for 'signalling gases', Nanotechnology 17 (2006) S48-S53, retrieved from the Internet on Mar. 19, 2016 at <URL: http://iopscience.iop.org/article/10.1088/0957-4484/17/4/008/meta;isessionid=DEE5CDBAODD81DDF45C9D0CA79F53344.c3>.

Helmus, Michael N., et al., Nanotechnology-enabled chemical sensors and biosensors. American Laboratory (2006) 38:34-38.

Murakami, Kazunari et al., Latest insights into the effects of *Helicobacter pylori* infection on gastric carcinogenesis. World J Gastroentero. (2006) 12:2713-2720.

Papatheodoridis, George V. et al., Effects of *Helicobacter pylori* and nonsteroidal anti-inflammatory drugs on peptic ulcer disease: a systematic review. Clin Gastroenterol Hepato. (2006) 4:130-142.

Sadek et al., "Polyaniline Nanofiber Based Surface Acoustic Wave Gas Sensors Effect of Nanofiber Diameter on H2 Response," IEEE Sensors Journal, vol. 7, No. 2, Feb. 2007, pp. 213-218.

Tveito, Kari et al., 13C-xylose and 14C-xylose breath tests for the diagnosis of coeliac disease. Scandinavian J. Gastroenterol 2008; 43(2): 166-763. SUNY State University of New York, Stony Brook. Taylor & Francis Ltd.

Waghuley et al., "Application of chemically synthesized conducting polymer-polypyrrole as a carbon dioxide gas sensor," Sensors and Actuators B, vol. 128, 2008, pp. 366-373.

He, Lifang et al., Gas Sensors for ammonia detection based on polyaniline-coated multi-wall carbon nanotubes (2009) Materials Science and Engineering B, 163:76-81.

Rana et al., "Influence of Previously Ingested Wheat on Fasting Breath Hydrogen in Celiac Patients," Dig. Dis. Sci., vol. 54, No. 6, 2009, pp. 1276-1279.

Hryniuk, Alexa et al., A Preliminary Investigation of Exhaled Breath from Patients with Celiac Disease Using Selected Ion Flow Tube Mass Spectrometry. J Gastrointestin Liver Dis. (2010) 19(1) pp. 15-20, Lakehead University , Thunder Bay, Ontario, Canada.

Lupan et al., "Selective hydrogen gas nanosensor using individual ZnO nanowire with fast response at room temperature," Sensors and Actuators B vol. 144, 2010, pp. 56-66.

*Nanomedicon, LLC* v. *Research Found. Of State Univ. of N.Y.*, 2012 NY slip Op 33742(U), Mar. 15, 2012, Supreme Court, Suffolk County, Docket No. 36815-2010, Judge: Emily Pines, 14 pages.

Biesiekierski, Jessica R. et al., No Effects of Gluten in Patients With Self-Reported Non-Celiac Gluten Sensitivity After Dietary Reduction of Fermentable, Poorly Absorbed, Short-Chain Carboydrates. Gastroenterology (2013) vol. 145, 12 pages.

Osorio-Fuente et al., "Submicrometric Fibrillar Structures of Codoped Polyaniline Obtained by Co-oxidation Using te NaClO/Ammonium Peroxydisulfate System: Synthesis and Characterization," J. Mex. Chem. Soc., vol. 57, No. 4, 2013, pp. 306-313.

Wang et al., "Effect of thermal treatment on conductometric response of hydrogen gas sensors integrated with HCl-doped polyaniline nanofibers," Materials Chemistry and Physics, vol. 144, 2014, pp. 155-161.

Decarbite®, P.W. Perkins Co., Inc., Safety Data Sheet (Jan. 5, 2015) 4 pages.

Giner Electrochemical (trace) Gas Sensors. Datasheet [online]. Giner, In.c, retrieved from the Internet on Apr. 22, 2016 at <URL: http://www.ginerinc.com/products.php?a=TGSI>.

Otsuka America Inc., BreathTek Urea Breath Test, retrieved from the Internet on Mar. 31, 2016 at <http://web.archive.org/web/20120228152952/http://www.otsuka-us.com/Products/Pages/BreathTek.aspx>, 2 pages.

Quest Diagnositics, *Helicobacter pylori* Urea Breath Test (UBIT), retrieved from the Internet on Mar. 20, 2016 at URL: http://www.questdiagnostics.com/hcp/topics/gastroent/hpylori_breath.html> 3 pages.

Sultan, et al. "A highly sensitive chlorine gas sensor and enhanced thermal DC electrical conductivity from polypyrrole/silicon carbide nanocomposites," RSC advances 6.87 (Aug. 29, 2016: 84200-84208. Abstract, p. 3 para 2; and p. 12 para 2.

Brown, L.M. *Helicobacter pylori*: epidemiology and routes of transmission. Epidemiol Rev (2000) 22:283-297.

Dutta, Ritaban et al., Classification of Ear, Nose and Throat Bacteria Using a Neural-Network-Based Electronic Nose; Mrs Bulletin, Oct. 2004, pp. 709-713, Materials Research Society http://www.mrs.org/publications/.

Gisbert, J.P., The recurrence of *Helicobacter pylori* infection: incidence and variables influencing it. A critical review. Am J Gastroenterol (2005) 100:2083-2099.

Hunt, R.H., Peptic Ulcer Disease: Defining the Treatment Strategies in the Era of *Helicobacter pylori*. Am J Gastroentero. (1997) 92:36S-40S; discussion 40S-43S.

Leung, Wai K. *Helicobacter pylori* and Gastric Neoplasia. Contrib Microbio (2006) 13:66-80.

Minoli, Giorgio et al., A Simplified Urea Breath Test for the Diagnosis of *Helicobacter pylori* Infection Using the LARA System. Laser Assisted Ratio Analyzer. J Clin Gastroenterol. (1998) 26:264-266; retrieved from the Internet on Mar. 28, 2016 at <URL: http://journals.lww.com/jcge/Abstract/1998/06000/.

O'Morain, Colm. Role of *Helicobacter pylori* in functional dyspepsia. World J Gastroentero. (2006) 12:2677-2680.

Romagnuolo, Joseph et al., Using Breath Tests Wisely in a Gastroenterology Practice: An Evidence-Based Review. Am J Gastroentero. (2002) 97: 1113-1126.

Sonnenberg, Amnon et al., The prevalence of Self-Reported Peptic Ulcer in the United States. Am J Public Health (1996) 86:200-205.

Tveito, Kari et al., A novel one-hour 13C-sorbitol breath test versus the H2-sorbitol breath test for assessment of celiac disease. Scandinavian J. Gastroenterol (2009) 44(7): 813-9. SUNY State University of New York, Stony Brook. Taylor & Francis Ltd.

Weir, Susan, et al., Recurrent Bacteremia Caused by a "Flexispira"-Like Organism in a Patient with X-Linked (Bruton's) Agam-

(56) References Cited

OTHER PUBLICATIONS maglobulinemia. J Clin Microbio (1999) 37:2439-2445. Retrieved from the Internet on Mar. 28, 2016 at <URL: http://jcm.asm.org>.

Gouma, et al., TiO2-based Gas Sensors as Thick or Thin Films: An Evaluation of the Microstructure. Proceedings of the International Symposium on Dielectric Ceramics, May 2-6, 1998 and Ceramic Transactions: Dielectric Ceramic Materials, (1999) vol. 100, pp. 419-428, The American Ceramic Society, Westerville, Ohio.

International Patent Application No. PCT/US2019/065556, International Search Report and Written Opinion mailed Apr. 8, 2020, 12 pages.

International Patent Application No. PCT/US2019/065556, Invitation to Pay Additional Fees mailed Feb. 12, 2020, 2 pages.

\* cited by examiner

BREATH ANALYZER DEVICES AND BREATH TEST METHODS

RELATED APPLICATIONS

This application is a U.S. National Phase Patent Application of International Patent Application No. PCT/US2019/065556, filed Dec. 10, 2019, which claims priority to U.S. Provisional Application No. 62/777,759, filed Dec. 10, 2018. The entirety of each of these applications is incorporated herein by reference.

FIELD OF THE INVENTION

The present application relates generally to a breath testing device and to methods of testing for multiple diseases of the gastrointestinal tract, the liver, the lungs, and the kidneys, along with testing for cancer, infections, and metabolic diseases. The present application also relates to a breath analyzer and breath test method for detecting both ammonia and carbon dioxide in a human breath sample to determine the presence of diseases in a subject's digestive tract. In some instances, the disease can include, but is not limited to, *H. pylori*.

INCORPORATION BY REFERENCE

This application incorporates by reference the entire contents of U.S. Patent Application Ser. No. 62/777,752, filed Dec. 10, 2018.

BACKGROUND OF THE INVENTION

Exhaled breath contains many gases and thousands of Volatile Organic Compounds (VOCs). Gases and VOCs in breath can be detected with the use of technologies like gas chromatography-mass spectroscopy (GC-MS), selected ion flow tube mass spectrometry (SIFT-MS), FTIR spectroscopy, ion mobility mass spectrometry, field asymmetric ion mobility spectroscopy, semiconductor chips, carbon nanotubes, metal oxides, doped and non-doped polymers and other types of conductive materials sensitive to various gases. Types of conductive materials are chemical sensitive field effect transistors or floating gate field effect transistors or any other field effect transistors. Other types of gas sensitive sensors are optical, electrochemical, thermochemical and surface acoustic wave (SAW) thin films deposited on conducting material (e.g., gold, platinum, palladium or other metals).

Gases in exhaled breath are mainly, oxygen ($O_2$) 16%, carbon dioxide ($CO_2$) 4%, nitrogen ($N_2$) 75% and water vapor (5%-6%). In addition the exhaled breath contains small amounts of argon, hydrogen ($H_2$), ammonia ($NH_3$), acetone, methanol, ethanol and methane ($CH_4$) which are some of the most commonly encountered organic volatile compounds. Other VOCs in exhaled breath are acetaldehyde, 2-propanol, acetonitrile, acrylonitrile, benzene, isoprene, pentane, methylexane, ethane, hydrogen sulfide, triethyl amine, trimethylamine, carbon disulfide, dimethyl sulfide, 1-Heptene, 1-Octene, 1-Nonene, 1-Decene, octane, nonene, dodecane, cyclohexane, 2-butane, indole, ester, carbon disulfide, pentane, nitric oxide (NO), ethane and propane. Breath VOCs are metabolic byproducts of physiologic or pathophysiologic processes taking place within the digestive tract, small and large intestine, in healthy or in diseased individuals.

Metabolomics

Metabolomics is the field which deals with the byproducts or metabolites of either physiologic or pathophysiologic processes within the human body. Such byproducts are, among others, the volatile organic compounds (VOCs) derived from breakdown of ingested substances by bacteria of the colon in healthy individuals and in individuals with diseases of the gastrointestinal tract, of the kidneys, of the lung, of metabolism, of the liver, and in individuals with cancer and infections. Analysis of VOCs and their patterns reflects the composition of microbiota and are considered to be markers of these diseases. Detection of VOCs is currently done using technologies such as gas chromatography-mass spectroscopy (GC-MS), selective ion flow tube mass spectrometry (SIFT-MS), field asymmetric ion mobility spectrometry (FAIMS) and electronic noses (e-Nose).

Technologies like GC-MS, SIFT-MS, and FAIMS are efficacious in detecting VOCs especially derived from colon microbiota. However, the instruments are expensive, large and mostly stationary. The e-Nose technology, a pattern recognition technology, uses various sensors which are less gas-selective and unstable. None of these technologies use individual sensors which detect each VOC in exhaled breath, and none of these instruments are small, hand-held, inexpensive and available for use over-the-counter (OTC) by exhaling in the instrument directly through an opening of the instrument or a through a mouthpiece. Metal oxide sensors either on their own or coupled with GC-MS are not optimal because the majority of them do not operate at room temperature and most of them need to be heated to about 450 degrees C. prior to use.

Celiac Disease and Non-Celiac Gluten Sensitivity

Celiac disease is an autoimmune enteropathy precipitated in susceptible individuals by the ingestion of gluten, specifically its immunotoxic component gliadin. Celiac disease enteropathy resolves with complete and lifelong gluten-free diet. Non-adherence or poor adherence to gluten-free diet may lead to small intestinal lymphoma, adenocarcinoma or other immunological diseases, such as diabetes, thyroiditis, hepatitis, etc. Individuals susceptible to celiac disease express autoantibodies such as antiendomysial and antitissue transglutaminase. In addition to those with confirmed Celiac disease, there are patients with subclinical or asymptomatic Celiac disease and family members of patients with Celiac Disease who have abnormal small intestinal histology without symptoms and who remain undiagnosed. The undiagnosed patients and those with delayed diagnosis remain on gluten-containing diet and risk serious damage to their intestinal mucosa and life-threatening consequences like cancer.

The prevalence of Celiac disease has been increasing in parts of the world, where consumption of gluten is common. Currently in the US, the prevalence of Celiac disease is 1%, much higher than its 0.02% prevalence in the early 1990s. There is also increasing prevalence of Non-Celiac Gluten Sensitivity, estimated at 3-6% in the US and Europe. Patients with Non-Celiac Gluten Sensitivity have no autoantibodies or intestinal mucosal changes of Celiac disease, but have similar symptoms with Celiac disease after ingestion of gluten which improve on gluten-free diet.

The current gold standard in the diagnosis of Celiac disease is small bowel biopsies of the small intestinal mucosa which are obtained through upper endoscopy. Patients with Celiac disease, who must follow a strict, lifelong gluten-free diet, undergo follow-up endoscopies with biopsies to assess adherence to gluten-free diet and the health of the small bowel mucosa. Other diagnostic methods exist, including blood tests for antiendomysial and antitransglutaminase antibodies. Currently there is no screening test for patients with symptomatic Celiac disease or with asymptomatic Celiac disease (subclinical Celiac disease and asymptomatic family members) who do not have the reason to undergo endoscopies. These asymptomatic patients however, are at high risk of developing co-morbidities consistent with those of symptomatic Celiac disease patients and potentially cancer. These asymptomatic patients who are mostly family members of patients with Celiac disease can benefit from certain embodiments of the present invention that offer a non-invasive breath test highly sensitive to the hydrogen in the breath after an eight to twelve (8-12) hour overnight fasting.

Helicobacter pylori (H. pylori) Infection

Helicobacter pylori (H. pylori), which affects two thirds of the world population, is a highly contagious, gram negative bacterium which causes chronic gastritis, peptic ulcers and can cause gastric cancer and other malignancies like gastric lymphoma (MALToma). It is associated with extraintestinal diseases like anemia, liver disease, gallbladder disease and pulmonary disease like asthma. One of the properties of H. pylori is its ability to hydrolyze urea into $CO_2$ and ammonia ($NH_3$) by using its abundant enzyme urease as in the following equation: $CO(NH_2)_2 + HOH$—urease→$CO_2 + 2NH_3$.

The gold standard in diagnosis of H. pylori is a $^{13}C$ urea breath test (UBT) which measures $^{13}CO_2$ in breath after ingestion of $^{13}C$ labeled urea as in the following equation: $^{13}CO(NH_2)_2 + HOH$—urease→$^{13}CO_2 + 2NH_3$. The current $^{13}C$ UBT requires the use of a relatively expensive kit and very expensive (several thousands of dollars) equipment which must be operated by professionals. There are other known methods to diagnose H. pylori infection, including: 1) upper endoscopy with biopsies and culture of the tissue; 2) upper endoscopy with biopsies and rapid urease test (CLO test); and 3) serum antibodies to H. pylori. Positive antibodies indicate infection with H. pylori. However, the antibodies remain positive even after eradication of the bacterium. As a result, the serum antibodies cannot be used to confirm eradication as the $^{13}C$ UBT (and the other methods) can. None of the existing diagnostic methods are inexpensive and hand-held, combining test and device in one.

Inflammatory Bowel Diseases (IBD)

Inflammatory bowel diseases are mainly Crohn's disease and Ulcerative colitis. There are differentiating features for each of these inflammatory bowel diseases as relating to 1) the part of the intestinal tract which is affected by inflammation in each of them (ulcerative colitis limited to the large intestine and Crohn's disease potentially affecting the entire digestive tract); 2) the histological changes in the intestinal mucosa; 3) the diagnosis; 4) the treatment; and 5) the prognosis.

The diagnosis of inflammatory bowel disease and the differentiation between Crohn's and ulcerative colitis is established with the use of endoscopies of the small and large intestine with biopsies and histological examination of the intestinal mucosa in addition to radiological studies (especially in the case of Crohn's disease). After the diagnosis is established, appropriate treatment is instituted. Such treatment is lengthy and requires periodic follow-up with endoscopies and biopsies to assess efficacy of the treatment.

It has been observed that changes in the colon-derived metabolome in patients with inflammatory bowel disease (Crohn's and ulcerative colitis) contribute to the development of a pattern of Volatile Organic Compounds (VOCs) in the breath of these patients. These VOCs are acetaldehyde, 2-propanol, acetonitrile, acrylonitrile, benzene, isoprene, pentane, methylexane, ethane, hydrogen sulfide, triethyl amine, trimethyl amine, carbon disulfide, dimethyl sulfide, 1-Heptene, 1-Octene, 1-Nonene and 1-Decene and others.

Small Intestinal Bacterial Overgrowth

Small intestinal bacterial overgrowth (SIBO) occurs in predisposed individuals and presents with symptoms similar to inflammatory bowel diseases such as abdominal pain, diarrhea, anemia and weight loss. The small bowel normally contains a very small number of microbes as compared to the large bowel, which normally contains several trillion of microbes (estimated at 100 billion per milliliter). SIBO occurs when bacteria, which normally ferment carbohydrates in the large bowel, migrate to the small bowel. As a result, fermentation of carbohydrates takes place in the small bowel, which in turn creates the symptoms of abdominal pain, steatorrhea, and abnormally high production of hydrogen which is absorbed and released through the lungs in the breath.

Conditions which predispose to the development of SIBO are anatomic abnormalities, abnormal motility of the intestine as in pseudo-obstruction, absence of the migratory motor complexes, autonomic neuropathy as in diabetes, excessive bacterial load as in achlorhydria, fistula and loss of the ileocecal valve and immunological problems like immunodeficiency and malnutrition.

Diagnosis of SIBO is obtained with invasive or non-invasive tests. Invasive tests include small bowel endoscopy and aspiration of content for culture for aerobic and anaerobic bacteria and motility studies. Non-invasive tests are 72 hour stool collection for fecal fat, serum bile acids and breath tests. The most common breath test is the hydrogen breath test after consumption of lactulose. Lactulose, a non-absorbable sugar, provides the substrate for the colonic bacteria to produce hydrogen which results in increased hydrogen levels in breath. If the large bowel bacteria are present in the small bowel then the hydrogen production after ingestion of lactulose occurs much earlier than usual and an early and late peak of hydrogen production is observed during the breath test. The gold standard hydrogen breath test is performed with the Quintron breath analyzer equipment. The individual undergoing breath testing for SIBO provides a baseline fasting breath sample and ingests a certain amount (about 7 g/Kg) of lactulose. In cases of SIBO, post-lactulose excretion of hydrogen gives two peaks, one early because large bowel bacteria are in the small bowel, and another peak later when the lactulose reaches the large bowel.

Irritable Bowel Syndrome

Irritable bowel syndrome (IBS) is a diagnosis of exclusion and is given to individuals who present with symptoms of abdominal pain, diarrhea or constipation, bloating and flatulence. IBS is a functional disorder of the digestive tract which, despite symptoms similar to IBD, has no organic etiology and no abnormality of the digestive tract has been associated with it. Intestinal motility abnormalities and food intolerance have been observed in certain individuals with IBS which can present with either diarrhea or constipation. Diagnosis of IBS is made after all organic causes for IBD, SIBO, infections and Celiac Disease have been ruled out. It is reported that analysis of fecal Volatile Organic Metabolites has a pattern consistent with IBS with diarrhea (IBS-D) which differentiates IBS-D from IBD and healthy individuals with a 94-96% sensitivity and 80-82% specificity. IBS-D fecal volatile organic compounds contain esters of short chain fatty acids such as cyclohexane carboxylic acids, butyrate, acetate and propionate. This observation can lead to developing the colon-derived breath metabolome as markers for IBS especially with diarrhea.

Lactose Intolerance and Fructose Intolerance

Lactose intolerance is intolerance to the lactose, the carbohydrate contained in milk. Lactose intolerance presents with symptoms similar to Irritable Bowel Syndrome and other malabsorption problems. The symptoms are abdominal pain, diarrhea and flatulence and occur after ingestion of milk or milk-containing products. Lactose is a disaccharide which is broken down to the monosaccharides glucose and galactose with the use of the enzyme lactase which is an enzyme present at the intestinal brush border. Glucose and galactose are easily absorbed and usually cause no symptoms. In individuals in whom the enzyme lactase is absent or severely limited, as in genetic conditions or post infections involving the digestive tract like, viral enteritis or parasitic or microbial infections, lactose is not metabolized and as a result it causes symptoms similar to carbohydrate malabsorption, diarrhea, abdominal pain, bloating and flatulence. Fructose intolerance is the inability to tolerate intake of fructose, the carbohydrate found in fruits. As a result, individuals with such inabilities who ingest fruits experience similar symptoms as the individuals with lactose intolerance. It is estimated that the adult human intestine can tolerate up to 25 g of fructose without symptoms. Ingesting more than 25 grams of fructose can cause diarrhea, flatulence and abdominal pain. Any amount of fructose can cause symptoms in individuals who have the genetic form of fructose intolerance due to genetic deficiency of the enzyme Aldolase B.

Liver Disease

Liver diseases are divided in two categories; genetic and inherited liver diseases and acquired liver diseases. The genetic and inherited liver diseases include disorders of carbohydrate metabolism, disorders of amino acid metabolism, abnormalities in mitochondrial fatty acid β-oxidation, α1-antitrypsin deficiency, disorders of the bile acid synthesis and metabolism, Wilson disease and others. The acquired liver diseases are mainly viral infections like hepatitis A, B, C and others which can lead to chronic hepatitis, cirrhosis and end-stage liver disease, Hepatocellular carcinoma (HCC) and other liver malignancies and diseases of the liver due to obesity, such as non-alcoholic liver disease (NALD) and non-alcoholic steatohepatitis (NASH) and metabolic abnormalities such as diabetes and others. Autoimmune hepatitis, which can lead to chronic hepatitis and cirrhosis, is an inflammatory hepatitis which is secondary to autoimmune diseases affecting more than one body organ. HCC can be the result of viral hepatitis and of steatohepatitis which is due to deposits of fat in its tissue. Steatohepatitis can be secondary to obesity, diabetes and alcoholic hepatitis. If untreated, steatohepatitis can lead to cirrhosis and end stage liver disease. Changes in metabolome have been observed in genetic liver diseases as well as in acquired liver disease and in end stage liver disease. Hyperammonemia is one of the symptoms of liver failure.

Renal Disease

Renal diseases are diseases of the kidneys and are genetic-idiopathic and acquired. Genetic diseases of the kidneys include several types of glomerulonephritis such as IgA nephropathy, Alport syndrome, Good pasture disease, membranous glomerulopathy, lupus-induced glomerulonephritis and others and anatomic abnormalities such as polycystic disease of the kidneys and UPJ obstruction. Acquired kidney diseases are post-infection glomerulonephritis such as acute post-streptococcal glomerulonephritis, hemolytic uremic syndrome (HUS), drug-induced glomerulonephritis, post-traumatic renal disease and others. Symptoms of renal disease are hematuria, proteinuria, edema and poor growth in children. When renal disease becomes chronic and progresses to renal failure (kidney failure), hemodialysis and eventual kidney transplant are essential. Hyperammonemia is a key feature of end stage renal failure due to the inability of the kidneys to excrete the accumulating ammonia.

Respiratory Diseases

More than 3,500 components make up the human breath and the majority are volatile organic compounds (VOCs) in very small amounts. In addition to nitric oxide (NO), which has become a biomarker for respiratory inflammation and asthma, a pattern of VOCs has emerged as prevalent within the population with allergic inflammatory component asthma. These compounds are nonane, 2,2,4,6,6-pentamethylheptane, decane, 3,6-dimethyldecane, dodecane, and tetradecane. The breath metabolome provides a characteristic of chronic obstructive pulmonary disease (COPD).

Metabolic Diseases-Cancer-Infections

Metabolic diseases like diabetes and obesity affect the metabolome. Increased levels of acetone in breath of individuals with diabetes, is a finding consistent with undiagnosed diabetes or poorly managed diabetes in individuals who are already diagnosed. The concentration of breath acetone has been found to correlate with the O-hydroxybutyrate concentration of venous blood in fasting obese patients. Studies have identified eight specific metabolites such as isopropanol and 2,3,4-trimethylhexane, 2,6,8-trimethyldecane, tridecane and undecane as a more specific pattern for the presence of type 2 diabetes with a high sensitivity and specificity. Increase in VOCs has been described in patients with various types of cancer such as colon, lung, breast and others. Infections involving the gastrointestinal tract such as bacterial infections (salmonella, shigella) and parasitic infections alter the colonic bacteria, and as a result, alter the corresponding breath metabolome.

*Helicobacter pylori* ("*H. pylori*") is a gram-negative bacterium found in the digestive tract that affects about two-thirds of the world's population. Most people contract *H. pylori* infection during childhood and may never have any signs or symptoms of the infection. However, when signs or symptoms do occur with *H. pylori* infection, they may include a burning pain in the abdomen and chest, nausea, vomiting, frequent burping, bloating and weight loss. *H. pylori* causes gastritis and the majority of peptic ulcers, and is associated with other intestinal diseases like inflammatory bowel diseases, hepatobiliary and pancreatic diseases. *H. pylori* is also associated with extraintestinal diseases, some of which are idiopathic thrombocytopenic purpura, iron deficiency anemia, renal diseases, and cardiovascular diseases like ischemic heart disease and atherosclerosis.

In addition, *H. pylori* was declared a Class I carcinogen for humans in 1994 by the International Association for Research on Cancer (IARC) and has been strongly associated with the development of gastric cancer and with gastric MALToma, a type of lymphoma. *H. pylori* has also been associated with other cancers like colon cancer and pancreatic cancer.

Current diagnostic methods for detecting *H. pylori* infection have several drawbacks. Some existing diagnostic methods include endoscopy with biopsies and bacterial culture. Such methods are expensive, uncomfortable, and carry risks for the subject to undergo. In addition, the results of such tests are not available until several days after the test has been performed. Furthermore, these invasive methods utilize large and expensive equipment operated by highly-trained personnel; require the use of either anesthesia, sedation, or both; and require the use of pathology and microbiology laboratories to render a diagnosis.

Currently available non-invasive methods for the detection of H. pylori include the $^{13}C$ labeled urea breath test; detecting H. pylori antigens in stool; a stool test for H. pylori DNA; and serum antibody testing. These known non-invasive methods are costly, not available for self-testing, and the testing results are unavailable until several hours or days after the test has been performed. Currently, these non-invasive methods utilize laboratory equipment for analysis of the breath sample for $^{13}CO_2$; to test blood for the H. pylori antibody; and to examine stool for the H. pylori antigen and/or for H. pylori DNA. All of these methods require expensive equipment and qualified personnel to carry out the particular testing method.

Urea breath tests are also known and have been used to detect H. pylori infection. In such known types of urea breath tests, the presence of H. pylori is based on the measurement of the ratio of $^{13}CO_2:^{12}CO_2$ in the breath of a subject after ingestion of a urea substrate labeled with $^{13}C$. The subject exhales into a bag, which is then attached to large equipment (e.g., a spectrometer) for analysis of the breath sample. If the $^{13}CO_2:^{12}CO_2$ ratio is above a certain value, the subject is considered positive for H. pylori. However, these known types of urea breath tests have several drawbacks. First, they use a urea substrate labeled with $^{13}C$, which, though it is a naturally occurring isotope of carbon, is very expensive in comparison to the also naturally occurring $^{12}C$ which is contained in the unlabeled urea. In addition, known urea breath tests require expensive instruments (e.g., infrared spectrometers) to analyze $^{13}CO_2$ and $^{12}CO_2$ levels.

As set forth in the present disclosure, it would be desirable to provide a breath test method that measures elevated levels of both ammonia and $CO_2$ (measured as $^{12}CO_2$ or $^{13}CO_2$; both $^{12}CO_2$ and $^{13}CO_2$; or as a ratio of $^{12}CO_2:^{13}CO_2$) in the breath of a subject before and after the subject ingests a urea substrate. It would also be desirable to provide such a breath test that can utilize a urea substrate regardless of whether the urea is labeled or unlabeled. In addition, it would be desirable to provide a reliable point-of-care diagnostic test that can be self-administered using a hand-held device to determine the presence of H. pylori. Still further, it would be desirable to provide an improved breath test that is less costly and more convenient than existing breath tests.

SUMMARY OF THE INVENTION

Certain embodiments of the present disclosure provide a universal, electrochemical multi-analyte breathalyzer device for the detection of gases in human breath of individuals with gastrointestinal, renal, respiratory, metabolic and inflammatory diseases, cancer, and infections. The universal electrochemical device can comprise a main body which houses multiple electrochemical sensors, the electronics to support the operation of the device, a power source, a USB port, and Bluetooth technology to transfer data wirelessly to another device or computer. The universal electrochemical device, which can have a display for input by the user and for output of the results, accepts the user's breath through either an opening of the body of the device (which acts as mouthpiece) or through a removable mouthpiece.

Certain other embodiments provide a breath analyzer that includes an input, a first sensor, a second sensor, a processor, and an electrical circuit. The input receives the breath sample. The first sensor contacts the breath sample and includes polyaniline and a conductive material. The polyaniline contacts the conductive material and is doped with a first dopant that increases pH sensitivity of the polyaniline. The polyaniline has a resistivity that increases in response to increased concentration of ammonia. The second sensor also contacts the breath sample. The second sensor includes polypyrrole and a conductive material. The polypyrrole contacts the conductive material and is doped with a second dopant that increases pH sensitivity of the polypyrrole. The polypyrrole has a resistivity that increases in response to increased concentration of carbon dioxide. The electrical circuit operably connects the first and second sensors to the processor. The processor detects resistivity in the electrical circuit and uses the resistivity to calculate a total concentration of ammonia and a total concentration of carbon dioxide in the breath sample.

Other embodiments provide a handheld, portable breath analyzer that includes a removable mouthpiece and a main body. The main body includes a first sensor, a second sensor, a processor, and an electrical circuit. The first sensor includes polyaniline, and the polyaniline is doped with a first dopant that increases pH sensitivity of the polyaniline. The polyaniline has a resistivity that increases in response to increased concentration of ammonia gas. The second sensor comprises polypyrrole, and the polypyrrole is doped with a second dopant that increases pH sensitivity of the polypyrrole. The polypyrrole has a resistivity that increases in response to increased concentration of carbon dioxide. The electrical circuit operably connects the first sensor and the second sensor to the processor. The processor detects resistivity of the first sensor and uses the resistivity to calculate a concentration of ammonia, and the processor detects resistivity of the second sensor and uses the resistivity to calculate a concentration of carbon dioxide.

Still other embodiments provide a breath test method. The breath test method includes the step of providing a portable breath analyzer that includes a removable mouthpiece and a main body. The main body includes a first sensor, a second sensor, a processor, and an electrical circuit. The first sensor includes ammonia selective material that has a resistivity that increases in response to increased concentration of ammonia gas. The second sensor comprises carbon dioxide selective material that has a resistivity that increases in response to increased concentration of carbon dioxide gas. The electrical circuit operably connects the first sensor and the second sensor to the processor, and the processor measure resistivity of the first sensor and the second sensor. The method further includes prompting a subject to exhale a baseline breath sample into the removable mouthpiece, and allowing the processor to measure a resistivity of the first sensor that occurs when the baseline breath sample contacts the first sensor. The method also includes prompting a subject to exhale a post-urea breath sample into the removable mouthpiece, and allowing the processor to measure a resistivity of the first sensor that occurs when the post-urea breath sample contacts the first sensor. Additionally, the breath test method includes the step of comparing the measured resistivity of the baseline breath sample to the measured resistivity of the post-urea breath sample.

Certain other embodiments provide a method of detecting presence of H. pylori in a digestive tract of a subject. The method includes collecting a baseline breath sample from a subject and determining a total amount of ammonia and a total amount of carbon dioxide present in the baseline breath sample. The method further includes collecting a post-urea breath sample from the subject, and determining a total amount of ammonia and a total amount of carbon dioxide present in the post-urea breath sample. Additionally, the method includes the step of designating a presence of *H. pylori* in the digestive tract if the total amount of ammonia and the total amount of carbon dioxide present in the post-urea breath sample exceeds the total amount of ammonia and the total amount of carbon dioxide present in the baseline breath sample by a predetermined value.

DETAILED DESCRIPTION OF PREFERRED EMBODIMENTS

Figure 1:
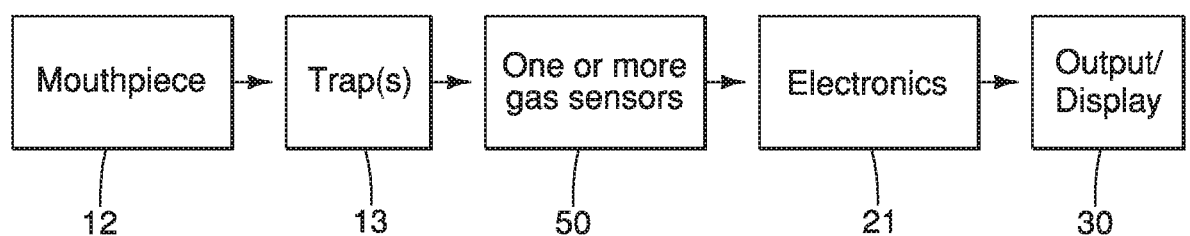
FIG. 1 shows a schematic of a breath analyzer according to an embodiment of the present disclosure.

The following detailed description is to be read with reference to the drawings, in which like elements in different drawings have like reference numerals. The drawings, which are not necessarily to scale, depict selected embodiments and are not intended to limit the scope of the invention. Skilled artisans will recognize that the examples provided herein have many useful alternatives that fall within the scope of the invention.

In certain embodiments, the present invention provides an improved breath analyzer and breath test method to determine the presence of *H. pylori* in a subject's digestive tract. The improved breath analyzer and breath test is less costly, more convenient, and more diagnostically accurate than existing methods and devices.

Exhaled human breath may contain 100 times more $CO_2$ than inhaled air. Exhaled $CO_2$ comes from various sources within the human body. One of these sources can be the presence of *H. pylori* in the gastrointestinal tract. Exhaled human breath contains about 3.8% $CO_2$ in healthy individuals who are not infected with *H. pylori*. $^{13}C$ is the naturally occurring isotope of elemental carbon. $^{12}C$ is the more stable isotope of carbon-12 and is in $CO_2$. $^{12}C$ exists in nature in abundance at 98.9% of the amount of element carbon. $^{13}C$, which is present in $^{13}CO_2$, is less abundant in nature and consists of only 1.1% of the natural element carbon.

H. pylori is a genotypically diverse bacterium that has the capacity to change its genetic makeup and mutate in vivo during colonization within a human subject's digestive tract. When H. pylori is positive for the cytotoxin-associated gene A (CagA), the risk for development of stomach cancer increases relative to when H. pylori is negative for CagA. In the western world, H. pylori seropositivity for CagA is approximately 60% as opposed to the Asian countries and most of Africa where the seropositivity for CagA approaches 100% within the H. pylori-affected population. The highly immunogenic CagA protein encoded by the CagA gene elicits serum antibody responses which can be detected by enzyme-linked immunosorbent assay (ELISA).

Despite differences in genetic makeup, all types of H. pylori are able to hydrolyze urea (either $^{13}C$ labeled or unlabeled) using its abundant enzyme urease to produce $CO_2$ (or $^{13}CO_2$) and ammonia ($NH_3$) gas. Once produced, ammonia and carbon dioxide ($CO_2$ or $^{13}CO_2$) are diffused in the bloodstream through the gastrointestinal mucosa and exhaled from the lungs through exhaled breath. The hydrolysis of urea, both in labeled and unlabeled form, is shown by Equations 1 and 2 below:

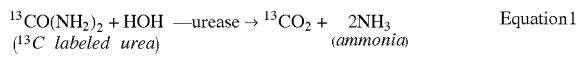

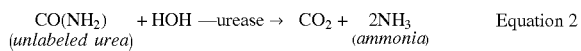

Prior urea breath tests require labeled urea substrates to detect the amount of labeled $CO_2$ in the breath. In contrast, the present breath analyzer and breath test method uses one or more sensors to detect the total amount of both ammonia and carbon dioxide present in a breath sample. Advantageously, the present breath analyzer and urea breath test method do not require a labeled substrate.

Figure 2:
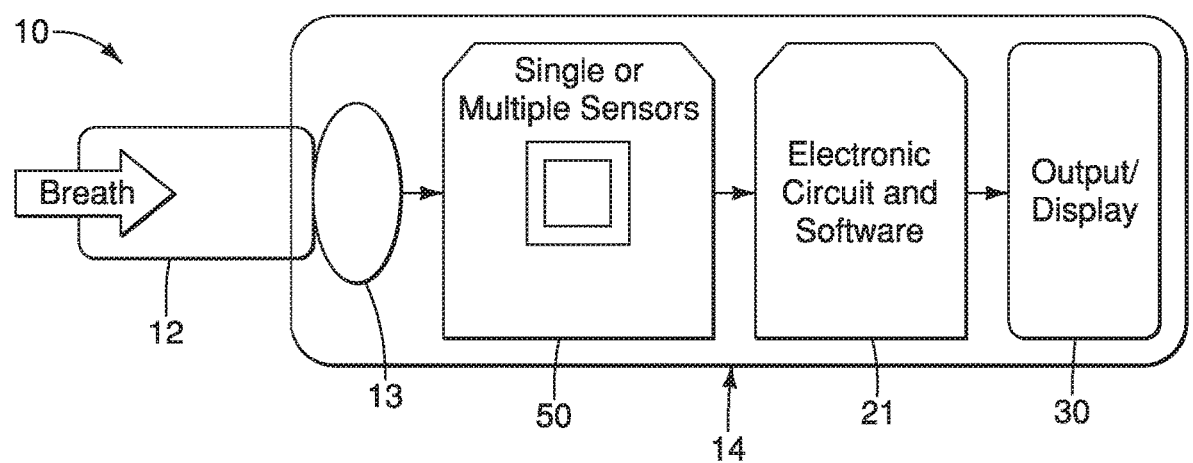
FIG. 2 shows another schematic of a breath analyzer according to an embodiment of the present disclosure.
Figure 9:
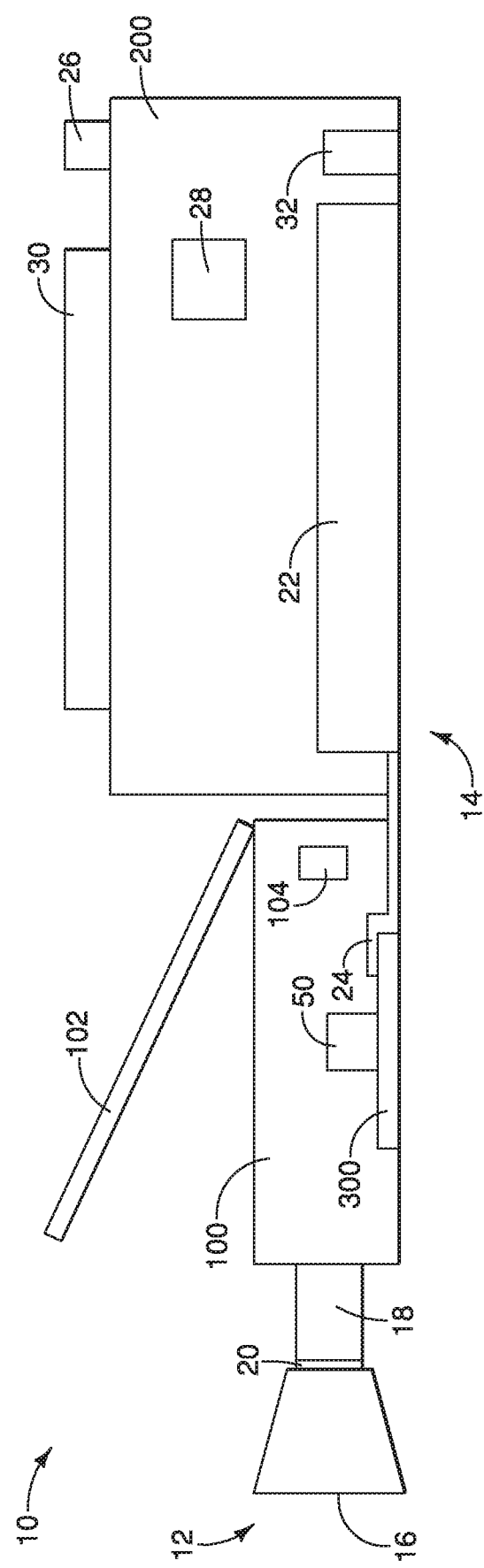
FIG. 9 shows a schematic of an embodiment of a breath analyzer.

Referring to the drawings, and in particular, FIGS. 1, 2, and 9, there are shown schematics of a breath analyzer 10 of the present disclosure. In some embodiments, the breath analyzer 10 includes some or all of the components depicted in these figures. In other embodiments, the breath analyzer 10 includes additional components, other than those depicted in these figures.

Certain embodiments of the breath analyzer 10 detect presence and concentration of both ammonia and carbon dioxide in a breath sample. As described in greater detail below, the breath analyzer includes an input, one or more gas sensors, an electrical circuit, and a processor. The input receives a breath sample. The at least one gas sensor contacts the breath sample. At least one of the one or more gas sensors includes ammonia selective material (e.g., doped polyaniline) and a conductive material. The electrical circuit operably connects the conductive material to the processor. The processor detects changes in resistivity in the electrical circuit and uses the changes in resistivity to calculate a concentration of ammonia in the breath sample. The same or a different gas sensor includes carbon dioxide selective material (e.g., doped polypyrrole) and a conductive material. The electrical circuit operably connects this conductive material to the processor. The processor detects changes in resistivity in the electrical circuit and uses the changes in resistivity to calculate a total concentration of carbon dioxide in the breath sample.

The breath analyzer 10 includes a mouthpiece 12 that has open ends to allow a breath sample to move therethrough. The mouthpiece 12 can comprise any suitable type of material, including, but not limited to, plastic or metal. The mouthpiece 12 includes a first portion 16 and a second portion 18. The first portion 16 is configured as an input that receives a breath sample. The first portion 16 can be sized and shaped to receive a user's lips, so that a user can blow exhaled breath into the mouthpiece 12.

In some cases, the mouthpiece 12 includes a one-way valve 20. In such cases, a user blows exhaled breath into the mouthpiece 12. The exhaled breath moves forward pass the one-way valve 20 and becomes trapped. In other words, the exhaled breath cannot move backward past the one-way valve 20 and toward the first portion 16.

The breath analyzer 10 also includes a main body 14. The mouthpiece 12 is attached to the main body 14. In particular, the second portion 18 of the mouthpiece 12 is sized and shaped to removably connect to the main body 14. For example, the second portion 18 can be snapped onto or perhaps screwed onto the main body 14. The main body 14 can comprise plastic, metal, or any other suitable material. In some cases, the main body 14 and the mouthpiece 12 comprise the same material. In other cases, the main body 14 and the mouthpiece 12 comprise different materials.

In certain embodiments, the mouthpiece 12 is a single-use mouthpiece. A single-use mouthpiece is desirable because it can be replaced for use with each new user. Also, in some cases, components of the mouthpiece 12 and/or main body 14 in contact with exhaled breath can be made of an inert or non-reactive material (e.g., polytetrafluoroethylene (PTFE)) that does not interfere with ammonia absorption.

The mouthpiece 12 can be integral with the main body 14, or can be a separate structure that is connected to the main body 14. In instances where the mouthpiece 12 is a separate structure connected to the main body 14, the mouthpiece 12 can be placed inside the main body 14 through a hole in the main body 14 using, for example, a push-in, screw-in, or tack-in motion.

In one embodiment, the mouthpiece 12 is permanently attached to the main body 14. In such instances, the mouthpiece 12 can be securely mounted on the main body 14, extending straight out from the main body 14 or at an angle from the main body 14. These alternate configurations allow the eyes of the subject taking the breath sample to either directly face the main body or to face away from main body 14 while taking the breath sample. The mouthpiece 12 can be permanently mounted to an opening in the main body 14 using a receptacle made of plastic or metal or any other material. In other cases, the mouthpiece 12 can be permanently attached to the main body 14 without the use of a receptacle.

Figure 10:
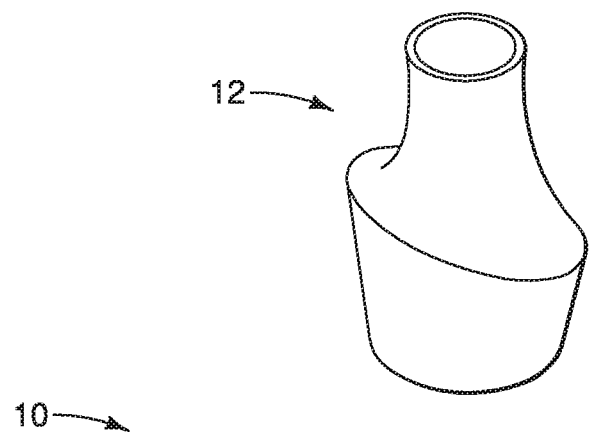
FIG. 10 shows an embodiment of a breath analyzer with a mouthpiece and a main body in a detached configuration.
Figure 10:
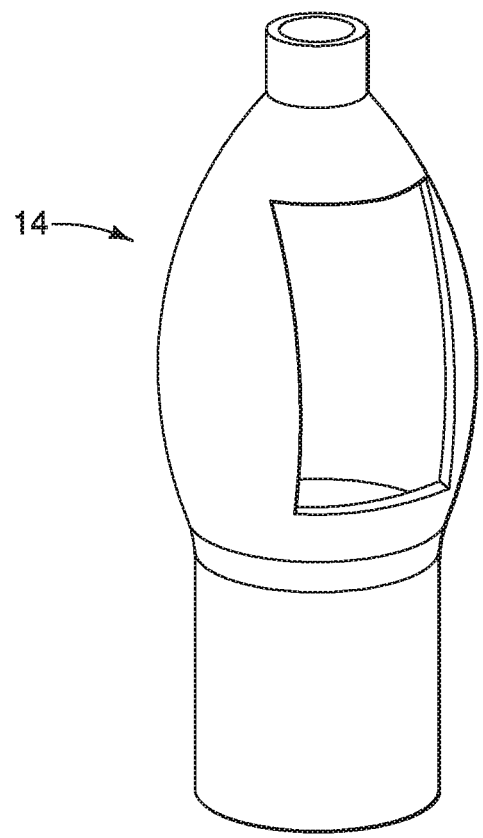
Figure 11:
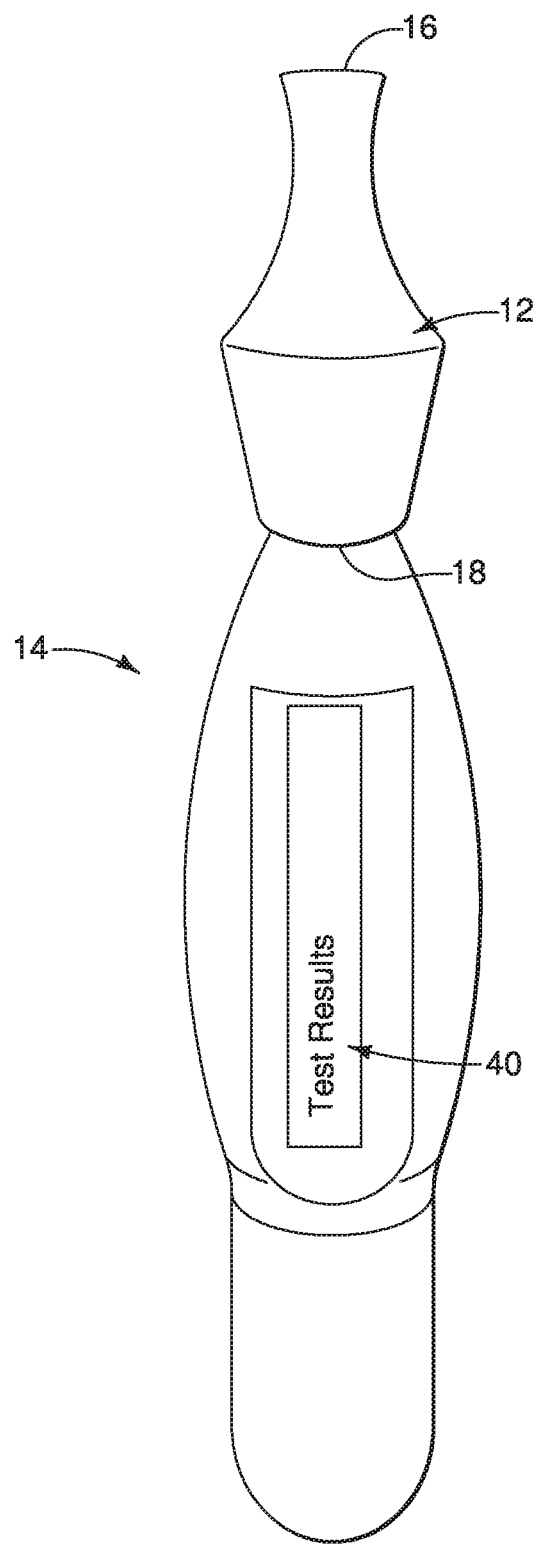
FIG. 11 shows an embodiment of a breath analyzer with a mouthpiece and a main body in an attached configuration.

FIGS. 10 and 11 illustrate an exemplary embodiment of the breath analyzer 10. FIG. 10 shows the breath analyzer 10 with the mouthpiece 12 attached to the main body 14, whereas FIG. 11 shows the breath analyzer 10 with the mouthpiece 12 detached from the main body 14. The breath analyzer 10 in these embodiments is provided as a self-contained, portable hand-held device. In some cases, the mouthpiece 12 is a single use mouthpiece that is disposed of after use, and that can be replaced with a new mouthpiece for each new user.

The mouthpiece 12 can be attached to an exterior of the main body 14 or can extend into the main body 14 of the breath analyzer 10. The mouthpiece 12 can be attached anywhere on or within the breath analyzer 10, provided that a first end 11 of the mouthpiece 12 is accessible to lips of the subject undergoing the breath test. The mouthpiece 12 can attach to the breath analyzer 10 via any suitable type of connection, including a straight connection, push-in connection, or screw-in connection, or have another type of connection within the main body 14 of the breath analyzer 10. In some cases, the mouthpiece 12 can be glued or can use any other type of adhesive to adhere the mouthpiece 12 to the main body 14.

The mouthpiece 12 can have any desired shape. For example, the mouthpiece 12 can be oblong, cylindrical, cone-shaped, or straw-shaped. The shape of the mouthpiece 12 should be such that the lips of the subject are able to wrap around the mouthpiece 12 in a tight manner. As disclosed above, the mouthpiece 12 can optionally include a self-sealing, one-way valve 20 to seal the breath sample from the surrounding air once the breath sample exits the mouthpiece 12 and enters the main body 14 of the breath analyzer 10.

The mouthpiece 12 can optionally include a lining material positioned inside of the mouthpiece 12. Where provided, the lining material covers some or all of an interior surface of the mouthpiece 12. In some cases, the lining material is a desiccant that can trap humidity. The desiccant can comprise (consist of, or consist essentially of) silica, activated charcoal, calcium sulfate, calcium chloride, or any other type of desiccant. The desiccant can also include a combination of any one or more of these or other desiccants. The desiccant can optionally have a color indicator to indicate the amount of humidity that the desiccant has trapped. In other instances, the mouthpiece 12 is devoid of any type of desiccant or other lining material.

In another embodiment, the mouthpiece 12 includes a lining material configured to trap and absorb some of the gases contained in a breath sample, while allowing other gases to go through. As an example, the lining material on the mouthpiece 12 can block $H_2O$, nitric oxide (NO), methane gas ($CH_4$), nitrogen gas ($N_2$), and other volatile organic compounds contained in human breath, while allowing $CO_2$ (or $^{13}CO_2$) and $NH_3$ to pass through the lining material and through the mouthpiece 12.

Figure 3:
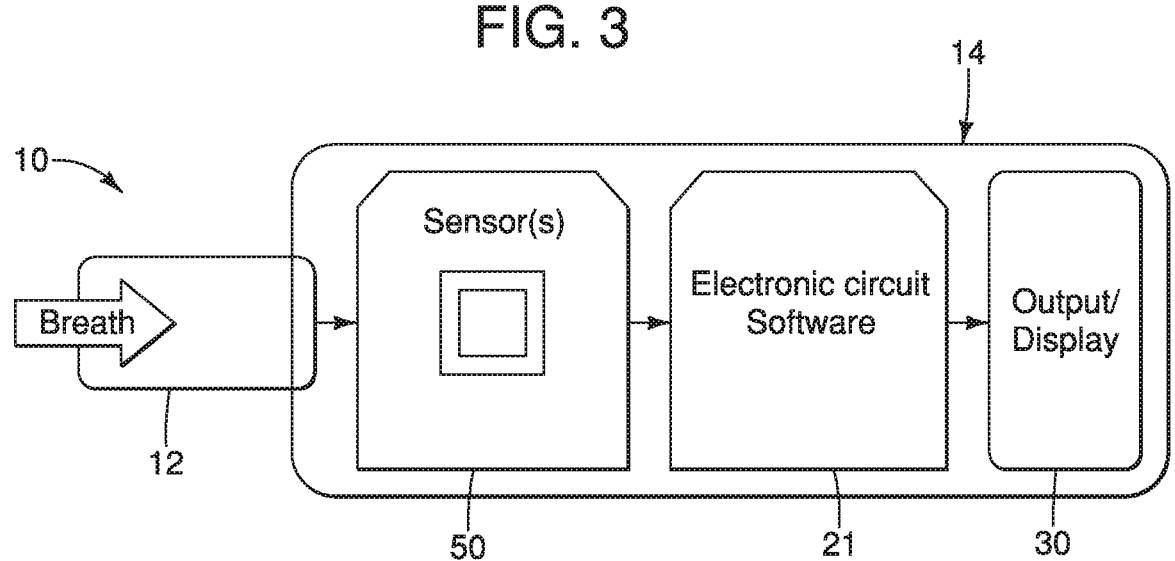
FIG. 3 shows a schematic of a breath analyzer according to yet another embodiment of the present disclosure.

The breath analyzer 10 can optionally include one or more filters 13 (or "traps"). The one or more filters 13 perform a similar function as the lining material for the mouthpiece 12. That is, the one or more filters 13 will allow certain gases to pass through, while trapping other gases and preventing them from passing through. The material for the one or more filters 13 can comprise sodium hydroxide, silica, activated charcoal, calcium sulfate, calcium chloride, or any other type of desiccant. The filter can also include a humidity sensor, such as a hygrometer. However, as shown in FIG. 3, in some cases, the breath analyzer 10 does not include any filters.

In one embodiment, the filter 13 is a single filter configured to block the passage of certain gases that are present in human breath and that are not intended to be measured by the breath analyzer 10. As an example, the filter 13 can block humidity, nitric oxide, methane, oxygen gas, and/or other volatile organic compounds present in a breath sample. This single filter allows the passage of ammonia ($NH_3$) and $CO_2$ and $^{13}CO_2$ or only ammonia or only $CO_2$ or only $^{13}CO_2$.

In another embodiment, the filter 13 comprises multiple filters. The filters 13 can have any desired shape and can comprise various types of materials. The shape of the filters 13 is not limiting, and can be round, oblong, square or a combination of different shapes. Each of these filters 13 can trap one or more of the undesirable gases (i.e., those gases not intended to be measured), and allow $CO_2$, $^{13}CO_2$ and ammonia to pass through, either separately or together.

Figure 7:
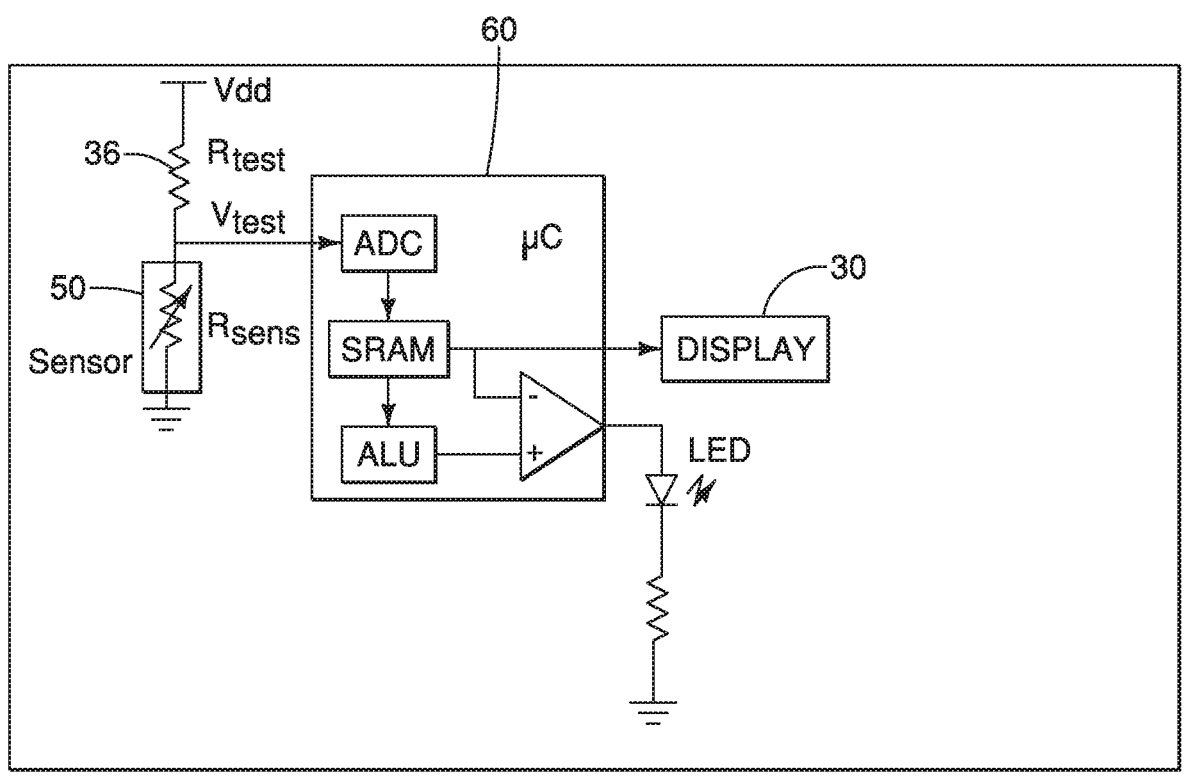
FIG. 7 shows an embodiment of an electrical schematic for the breath analyzer.
Figure 8:
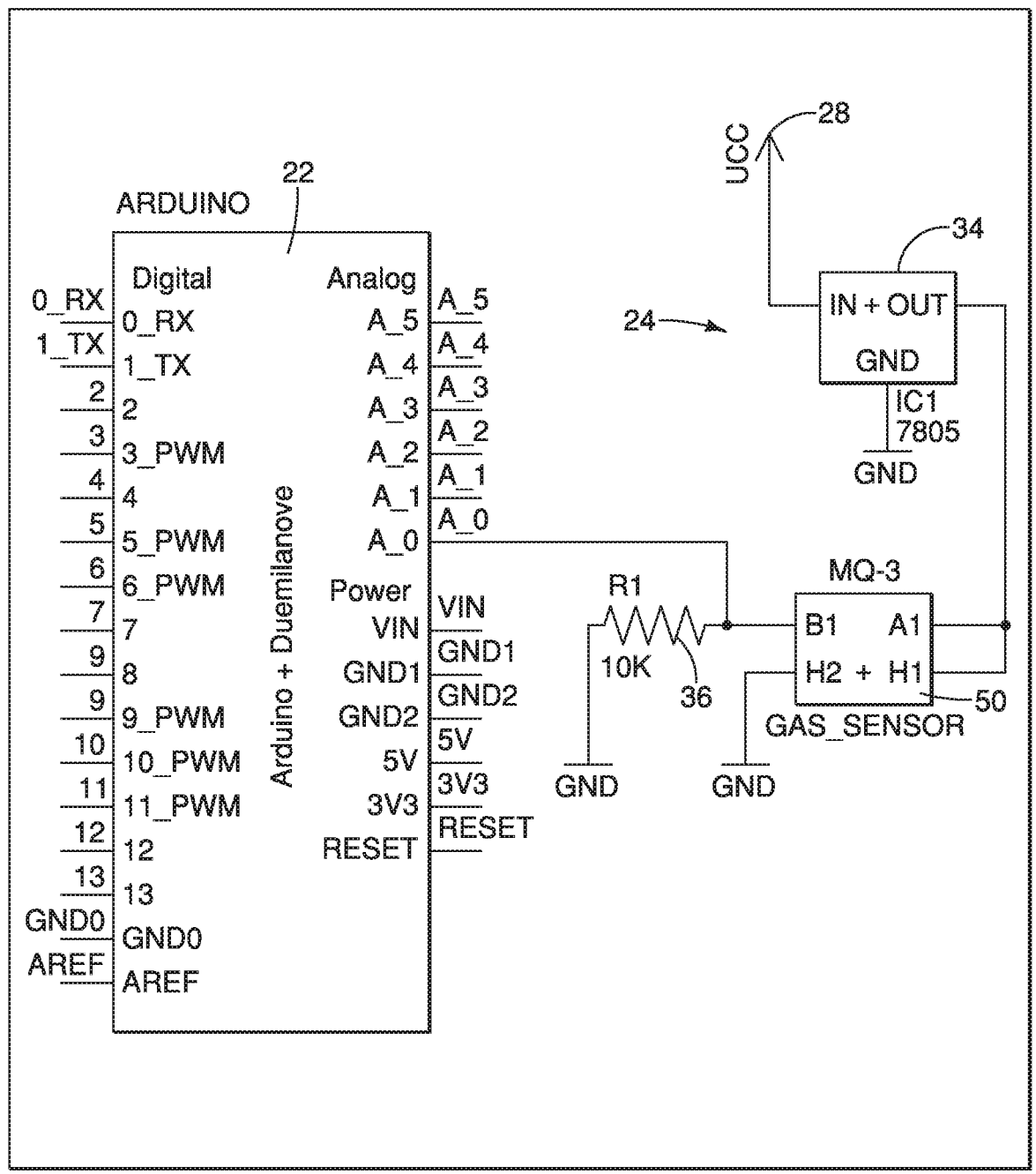
FIG. 8 shows another embodiment of an electrical schematic for the breath analyzer.

The breath analyzer 10 includes at least one gas sensor 50, a processor 22 and a power source 28. FIGS. 7 and 8 are electrical schematics illustrating the electrical connection between these components according to two embodiments. As shown, the at least one sensor 50, processor 22 and power source 28 are electrically connected via an electrical circuit 24.

The processor 22 can be any desired processor known in the art. In some cases, the processor 22 is a microcontroller. In certain cases, the processor 22 is an Arduino microcontroller.

Figure 4:
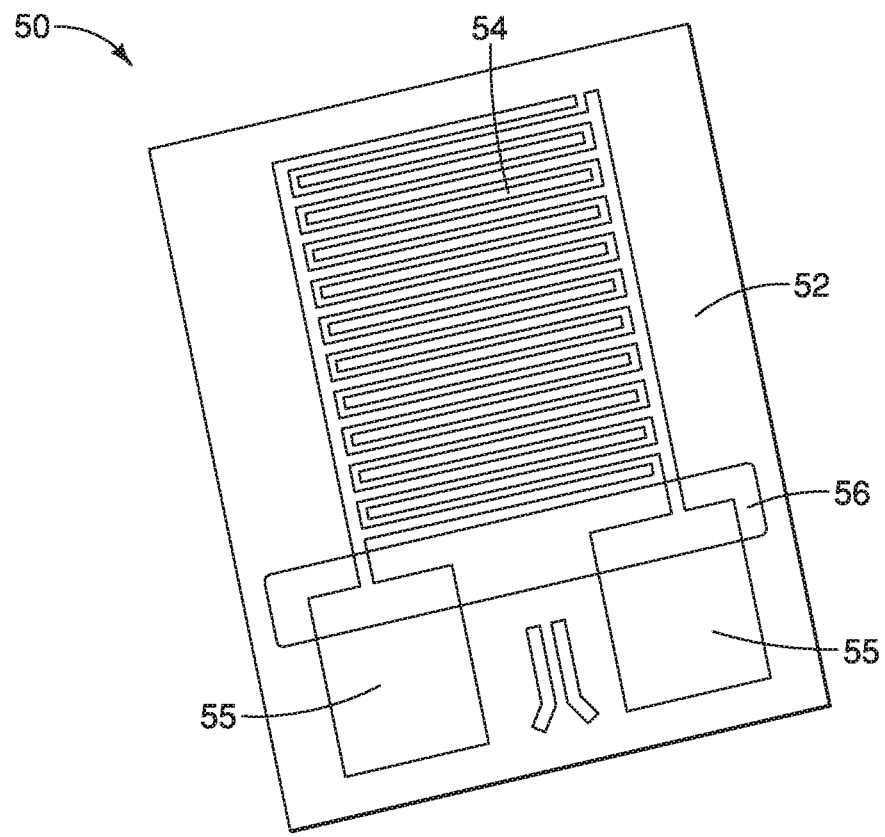
FIG. 4 shows an embodiment of an ammonia sensor.
Figure 5:
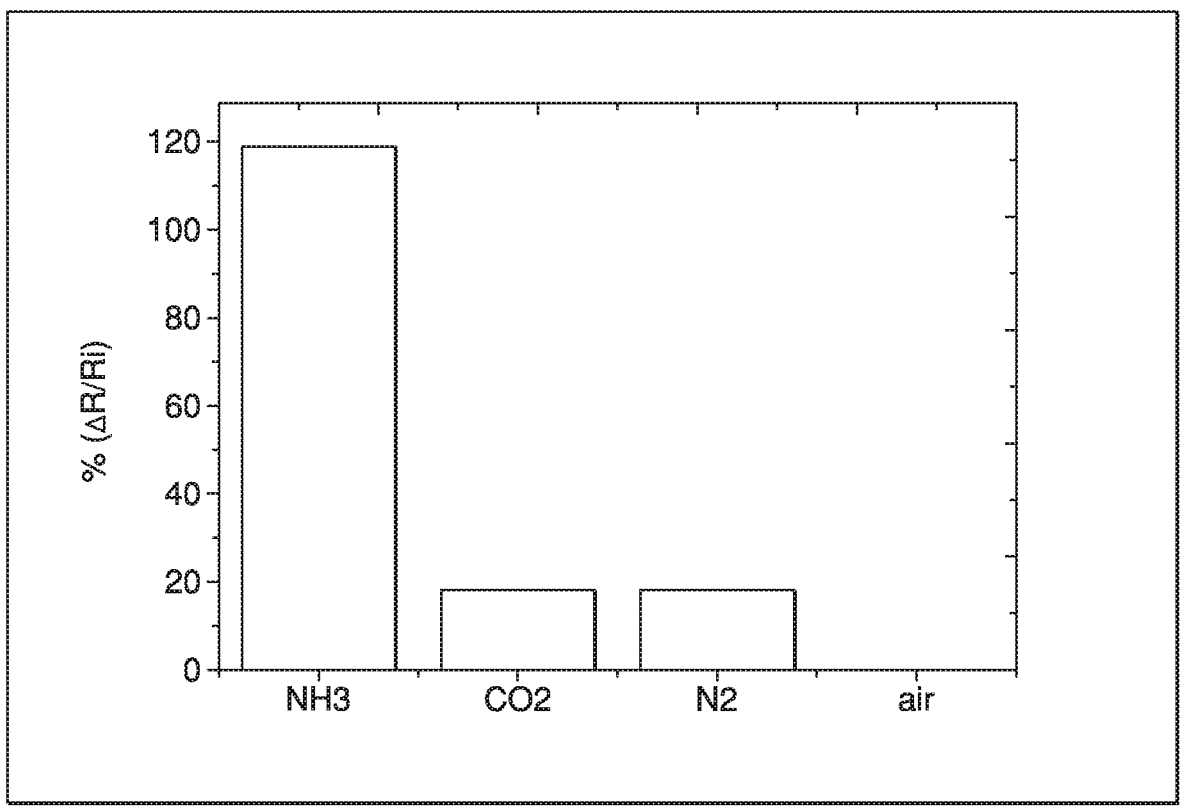
FIG. 5 is a graph showing a change in resistivity of a polyaniline-CSA sensor when the sensor comes into contact with pure gas.

The at least one sensor 50 can have any of the embodiments already described. In some cases, the at least one sensor 50 includes the sensor 50 shown in the embodiment of FIG. 4. The at least one gas sensor 50 is electrically connected to the electrical circuit 24 using any desired connection mechanism. In some cases, the at least one sensor 50 connects to the electrical circuit 24 via an optional sensor mount 300. In such cases, the at least one sensor 50 can be mounted directly onto the sensor mount 300. The sensor mount 300 serves as an interface between the sensor 50 and the electrical circuit 24. Thus, the sensor mount 300 can be any structure known in the art that connects the electrodes of the at least one sensor 50 to the electrical circuit 24. In some embodiments, the sensor mount 300 is a printed circuit board.

In other cases, the at least one sensor 50 is directly connected to the electrical circuit 24. For example, in some embodiments, the electrical circuit 24 includes two metal clips that can be clamped onto the contact pads 54 to create an electrical connection. A user can also replace an old sensor 50 with a new sensor by pulling the old sensor 50 out of the metal clips and inserting a new sensor 50 into the clips.

The main body 14 also includes an on/off button 26 and the power source 28. The power source 28 can be a portable power source, such as a battery. When the on/off button 26 is activated, the power source 28 turns on. As shown, for example in FIG. 7, the power source 28 supplies voltage to a voltage regulator 24. In certain cases, the power source 28 supplies 9 volts to the voltage regulator 24. The voltage regulator 24 regulates the amount of voltage sent to the sensor 50. In some cases, the voltage regulator 24 supplies a voltage to the at least one sensor 50 in the amount of between 0 volts to 5 volts. In certain cases, the voltage regulator 24 supplies a voltage to the at last one sensor 50 in the amount of about 5 volts. In one embodiment, the voltage regulator 24 is an IC1 7805 voltage regulator, a product manufactured by Fairchild Electronics.

A resistor 36 is also electrically connected to the at least one sensor 50 and provides resistance to the at least one sensor 50. In some case, the resistor 36 is a 10 kΩ resistor. When the breath sample contacts the at least one sensor 50, a change in resistivity occurs in the sensor 50 that correlates to an amount of ammonia and/or amount of carbon dioxide present in the sample. The at least one sensor 50 outputs voltage (along with the changes in resistivity) to the processor 22. The processor 22 detects changes in resistivity in the at least one sensor 50 and uses the changes in resistivity to calculate a concentration of ammonia and carbon dioxide in the breath sample. The processor 22 can also compare a concentration of ammonia between two different breath samples. Similarly, the processor 22 can compare a concentration of carbon dioxide between two different breath samples.

The gas sensor 50 can comprise a single gas sensor or more than one gas sensor. Each gas sensor 50 is configured to detect and measure one or more of ammonia, $CO_2$, and $^{13}CO_2$ in a human breath sample. Thus, at least one gas sensor 50 is sensitive to ammonia ($NH_3$), at least one gas sensor 50 is sensitive to $CO_2$, and at least one gas sensor 50 is sensitive to $^{13}CO_2$. For example, one gas sensor 50 can be sensitive to ammonia, a different gas sensor 50 can be sensitive to $CO_2$, and yet a different gas sensor 50 can be sensitive to $^{13}CO_2$. Alternatively, a single gas sensor 50 can be sensitive to any combination of these gases. As an example, one gas sensor 50 can be sensitive to ammonia and to $CO_2$ and to $^{13}CO_2$; another gas sensor 50 can be sensitive to ammonia (and not to $CO_2$ or $^{13}CO_2$); and another gas sensor 50 can be sensitive to $CO_2$ and to $^{13}CO_2$ (and not to ammonia). One or more of gas sensors 50 can measure the humidity in breath to assess its effect on the sensitivity of the gas sensor 50 to the particular gas under detection.

The breath analyzer 10 can measure ammonia and $CO_2$ (including $^{12}CO_2$, $^{13}CO_2$, and/or both $^{12}CO_2$ and $^{13}CO_2$) either simultaneously or in succession. Where the breath analyzer 10 measures ammonia and $CO_2$ in succession, the measurements occur within a short period of time (e.g., from about 1-10 seconds) of each other. This enables the breath analyzer 10 to measure and process the effect of each gas sensor 50 simultaneously or nearly (i.e., substantially) simultaneously.

Each gas sensor 50 includes a substrate 52, an electrically-conductive material 54, and a gas-selective material 56. The electrically-conductive material 54 is deposited onto the substrate 52. The electrically-conductive material 54 can comprise (consist of, or consist essentially of) any desired electrically-conductive material. In some cases, the electrically-conductive material 54 is platinum. In other cases, the electrically-conductive material 54 is gold.

In certain embodiments, the electrically-conductive material 54 is an electrode arrangement. The electrode arrangement can be a single electrode or a plurality of electrodes. The electrodes can be spaced apart in any desired arrangement. In some cases, the electrodes are spaced less than about 250 μm apart, perhaps less than about 150 μm apart, such as about 100 μm apart. In certain cases, the electrodes are spaced less than about 10 μm apart, such as 5 μm apart. In some embodiments, such as the gas sensor 50 shown in FIG. 4, the electrodes include interdigitated finger electrodes. In one embodiment, the gas sensor 50 comprises interdigitated platinum finger electrodes with a line spacing of 100 μm apart or less.

The one or more gas sensors 50 can operate at room temperature (i.e., 68-77° F., or 20-25° C.) or at a higher temperature. The one or more gas sensors 50 can be fabricated by any suitable method. Such methods can include spin coating, drop-coating, sol-gel, or any other known fabrication method. The one or more gas sensors 50 can be fabricated for either single use or for multiple, repeated uses. The one or more gas sensors 50 can comprise polyaniline or polypyrrole doped with a protonic acid. As non-limiting examples, the one or more gas sensors 50 can comprise PANI/CSA (polyaniline/camphorsulfonic acid); PANI/DNNSA (polyaniline/dinonylnapthalenesulfonic acid); or PPY/DBSA (polypyrrole/dodecylbenzynesulfonic acid). Applicant has found that a PANI/CSA gas sensor can be sensitive to detecting ammonia, and further that PANI/DNNSA and PPY/DBSA can be particularly sensitive to detecting $^{12}CO_2$ and/or $^{13}CO_2$.

The one or more gas sensors 50 can comprise thin-film or thick-film sensors capable of sensing ammonia gas ($NH_3$) and/or carbon dioxide gas ($CO_2$ and/or $^{13}CO_2$) simultaneously or in succession. Such gas sensor or sensors 50 can comprise polymer-thin film or polymer-thick film or polymer composite film. The one or more gas sensors 50 can be metal oxide sensors such as zinc oxide (ZnO) or other metal oxide sensors. The one or more gas sensors 50 can be a blend of polymer with metal oxide (such as polyaniline, polypyrrole, or another polymer, in combination with zinc oxide, or another metal oxide). In some cases, the one or more gas sensors 50 comprise sulfonated polyaniline or polyethylenimine (PEI) blended with polyelectrolytes. In other cases, the one or more gas sensors 50 can be emeraldine-base polyaniline (EB-PANI) blended with poly(3,4-ethylenedioxythiophene) polystyrene sulfonate (PEDOT:PSS).

In some cases, the ammonia selective material 56 includes doped polyaniline. Polyaniline exhibits three different oxidation states: leucoemeraldine (LEB, fully reduced), emeraldine (EB, half-oxidized), and pernigraniline (PNB, fully oxidized). Also, when polyaniline is in the emeraldine state, it can be in either an emeraldine salt or emeraldine base form. When in the emeraldine salt form, the polyaniline is conducting. The emeraldine salt form is usually obtained by protonating the basic amine and imine sites with strong acids. This process is reversible in that the emeraldine base form is obtained by deprotonating the amine groups. Thus, the emeraldine state of polyaniline transitions between an acid form and base form.

The inventor has discovered that the acid-base transition of polyaniline renders it pH sensitive and this characteristic allows it to be effectively used in ammonia detection. When ammonia contacts an emeraldine salt form of polyaniline, the ammonia deprotonates the amine groups and converts it to an emeraldine base, which also causes an increase in resistivity and a corresponding decrease in conductivity.

In some case, the one or more gas sensors 50 can include a dopant to increase sensitivity of the gas sensor 50. For example, where polyaniline is used for the at least one gas sensor 50, the polyaniline can be doped with a protonic acid to increase its pH sensitivity. Polyaniline with increased pH sensitivity is desirable for ammonia detection because when ammonia converts the polyaniline to an emeraldine base, it causes an even larger increase in resistivity and corresponding decrease in conductivity. Larger increases in resistivity (and decreases in conductivity) are desirable because they are easier to detect, and thus increase the sensitivity of the polyaniline to ammonia.

Polyaniline doped with a protonic acid has increased pH sensitivity compared to undoped polyaniline. In some cases, the polyaniline can be doped with a protonic acid including ions such $Cl^-$ and $SO_4^{2-}$ to obtain pH sensitivity of around 59 mV. Certain protonic acids cause an even larger increase in pH sensitivity. For example, polyaniline doped with camphor sulfonic acid has been shown to have a pH sensitivity of around 70 mV.

In some cases, the polyaniline comprises at least one dopant that increases pH sensitivity of the polyaniline. In some cases, the dopant is a protonic acid. In some embodiments, the dopant is hydrocholoric acid. In other embodiments, the dopant is camphor sulfonic acid. In yet other embodiments, the dopant is both hydrocholoric acid and camphor sulfonic acid. Other possible dopants include, but are not limited to, sulfuric acid, salicylic acid, acetic acid, citric acid, tartaric acid, oxalic acid, malonic acid, succinic acid, glutamic acid, adipic acid and phthalic acid. Also, in some cases, the polyaniline has a dopant that provides the polyaniline with a pH sensitivity of more than 59 mV. In one embodiment, the polyaniline has a camphor sulfonic acid dopant, which provides the polyaniline with a pH sensitivity of about 70 mV, which is a higher sensitivity observed than when using other dopants.

Also, the gas-selective material of the gas sensor 50 can be deposited directly onto the electrically-conductive material using any desired deposition process. For example, the gas-selective material can be deposited onto the electrically-conductive material using a spin coating method, a drop coating method, a chemical vapor deposition method, or a sputtering method. In certain cases, the electrically-conductive material is coated with spun cast gas-selective material. In certain embodiments, the gas-selective material is doped polyaniline deposited directly onto the electrically-conductive material using a spin coating method.

As discussed above, the one or more gas sensors 50 can detect and measure one, two, or more than two gases. At least one of the one or more gas sensors 50 detects ammonia gas ($NH_3$) at very low ppb levels. In some cases, the one or more gas sensors 50 detect ammonia concentration levels in a range from 1 ppb up to 1 ppm. In some cases, the one or more gas sensors 50 detect ammonia gas in a concentration range of 10 ppb and higher (e.g., in a range of from about 10 ppb up to about 50 ppb), or in a concentration range of 500 ppb or higher. In still other cases, the one or more gas sensors 50 detect breath ammonia at levels lower than 50 ppb and as high as 500 ppm.

Figure 6:
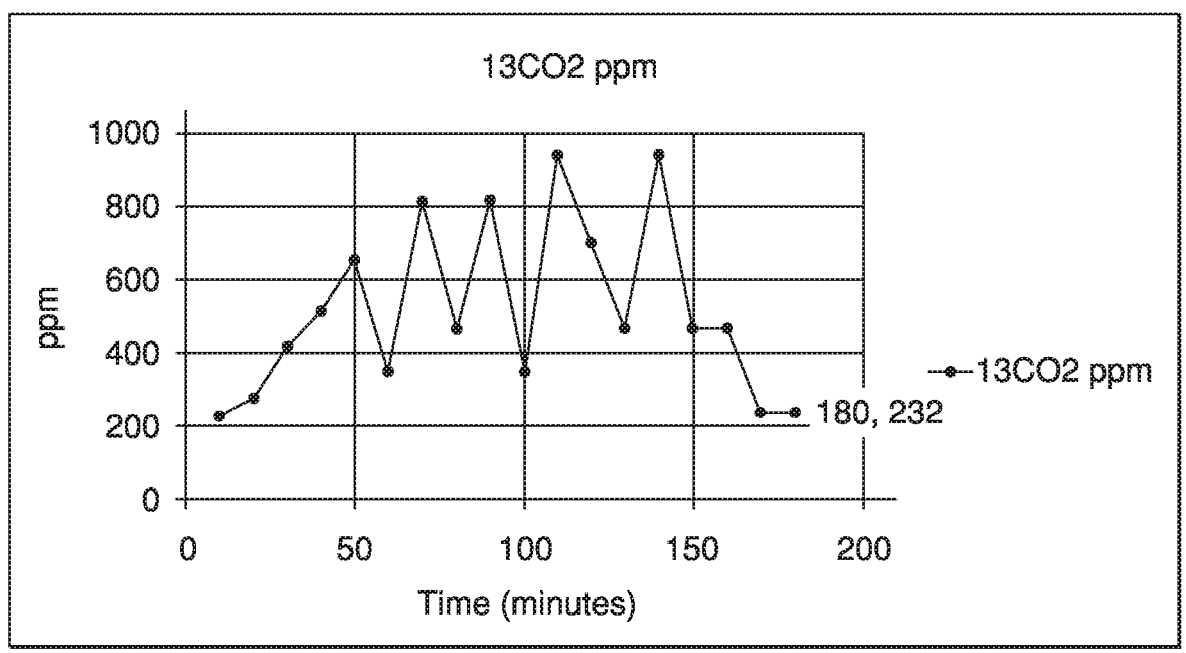
FIG. 6 is a graph showing measurement of $^{13}CO_2$ concentration in breath samples of multiple subjects, after the subjects ingested a high-protein meal followed by 5 mg/kg of $^{13}C$-labeled urea.

As noted above, at least one of the one or more gas sensors 50 detects $CO_2$. The $CO_2$ detected can be $^{12}CO_2$, $^{13}CO_2$, or the ratio of $^{13}CO_2$:$^{12}CO_2$. In some cases, at least one of the gas sensors 50 detects $CO_2$ (or $^{13}CO_2$) at concentrations in a range of 10 ppm-1500 ppm and higher (FIG. 6). In some cases, the at least one gas sensor 50 detects $CO_2$ at levels as low as 1 mM/min or 50-100 ppm. In addition, in some cases, the at least one gas sensor 50 detects $^{13}CO_2$ at levels as low as low as 1 mM/min or 50-100 ppm.

The one or more gas sensors 50 can comprise thin film polyaniline (PANI) doped with hydrochloric acid (HCl). Such a sensor can be prepared by chemical oxidative polymerization of aniline in aqueous acidic medium (1M HCl) with ammonium persulfate (APS) as an oxidant. The PANI sensor can be doped with acid dopants other than HCl. In some cases, the one or more gas sensors 50 can comprise thin film polyaniline doped with camphorsulfonic acid (PANI-CSA) and further doped with HCl or another acid dopant.

In some cases, the one or more gas sensors 50 can comprise thick film polymer pyrrole. Such sensors can be polymerized in the presence of an oxidant such as $FeCl_3$ or any other acid. Polymerized pyrrole (polypyrrole) can detect and measure $CO_2$ and $^{13}CO_2$ at concentration levels of 10 ppm and above.

In certain instances, the one or more than one gas sensors 50 can comprise a fiber optic sensor capable of sensing ammonia, $CO_2$ and/or $^{13}CO_2$. It is envisioned that other gas sensors 50, other than those specifically mentioned herein, can be used as the one or more gas sensors 50 to detect and measure ammonia, $CO_2$, and $^{13}CO_2$.

One non-limiting method for fabricating a PANI-CSA thin-film sensor is the following: The films can be prepared by spin coating the PANI-CSA solution on interdigitated array (IDA) electrodes. Prior to spin coating, the electrodes can be cleaned by rinsing in methanol followed by rinsing with deionized water and drying in a stream of dry nitrogen. PANI films can then be spun cast onto the IDA electrodes by adding 100 μl solutions at 500 RPM. The electrode pads can be cleaned, e.g., with a Q-tip dipped in methanol, to facilitate direct electrical contact with the breath analyzer 10.

The breath analyzer 10 further includes contact pads 55 and an electronic circuit 60. The one or more gas sensors 50 are connected to the electronic circuit 60 via the contact pads 55. The electronic circuit 60 is electrically connected to the one or more gas sensors 50. The electronic circuit 60 can function as shown in FIG. 7, or can function as shown in FIG. 8. The electronic circuit 60 can register multiple successive values for each measured gas detected by the one or more gas sensors 50. In some cases, the electronic circuit 60 will register the highest detected value or the average value for each gas detected by the one or more gas sensors 50. Through the use of software, the electronic circuit 60 will convert the measured resistivity of the gases into concentrations (ppb for ammonia and ppm for $^{13}CO_2$ and $CO_2$).

In some embodiments, the breathalyzer 10 includes a display 30. The display 30 is electrically connected to the processor 22. The display 30 is configured to visually display the amount of ammonia, $CO_2$, and $^{13}CO_2$ gas detected by the one or more gas sensors 50. The display 30 can be a window display provided on the main body 14 of the breath analyzer 10. In an alternative embodiment, the results can be displayed, with the use of Bluetooth technology or any other wireless data transmitter, through a computer portal or other device that can be either stationary or portable.

The display 30 can display a single result that represents the additive result of all three gases (ammonia, $^{13}CO_2$ and $CO_2$) or can display one result for each respective gas (i.e., one output for ammonia, one output for $CO_2$, and one output for $^{13}CO_2$). In some embodiments, the results are displayed in numerical values (e.g., from 1-1000, where a value of 1 represents no *H. pylori* infection, and a value of 1000 represents a subject infected with *H. pylori*) and/or in actual units of measured gases (e.g., ammonia concentration in ppb; and $CO_2$ and/or $^{13}CO_2$ concentration in ppm). In other embodiments, the results can be displayed as a yes or no indication, and/or in color using a light source. For example, green light on the display 30 can represent a negative test result and red light on the display 30 can represent a positive test result. Any one or more of these results (e.g., numerical values, actual units of measured gases, color, yes/no indication) can be displayed on the display 30.

In some embodiments, the main body 14 is configured as including a first compartment 100 and a second compartment 200. In some cases, as shown in FIG. 9, the first compartment 100 is a chamber that houses the at least one gas sensor 50 and a sensor mount 300, and the second compartment 200 is an electrical housing that houses various components. In certain embodiments (not shown), a separate chamber can be provided for each of the at least one gas sensor 50.

In some cases, the chamber 100 includes a lid or door 102 that opens and shuts. When the door 102 is closed, the chamber 100 provides a closed, sealed environment around the at least one sensor 50. When the door 102 is open, the at least one gas sensor 50 is accessible through the door opening. A user can open the chamber door 102 to remove and replace the at least one sensor 50 as needed. The chamber 100 also includes an outlet 104. The outlet 104 includes a cap that can be opened to release a breath sample from the chamber 100 and closed to trap a breath sample within the chamber 100.

The mouthpiece 12 is connected to the chamber 100 such that exhaled breath passes from the mouthpiece 12 directly into the chamber 100. As discussed above, the breath analyzer 10 can include a filter 13. In some cases, the filter 13 is a desiccant assembly 60. The desiccant assembly 60 helps to remove excess moisture from the exhaled breath. In some embodiments, the desiccant assembly 60 is provided inside of the mouthpiece 12. In other embodiments, the desiccant assembly 60 is provided inside of the chamber 100. Exhaled breath first moves through the desiccant assembly 60 before coming into contact with the at least one gas sensor 50.

Figure 12:
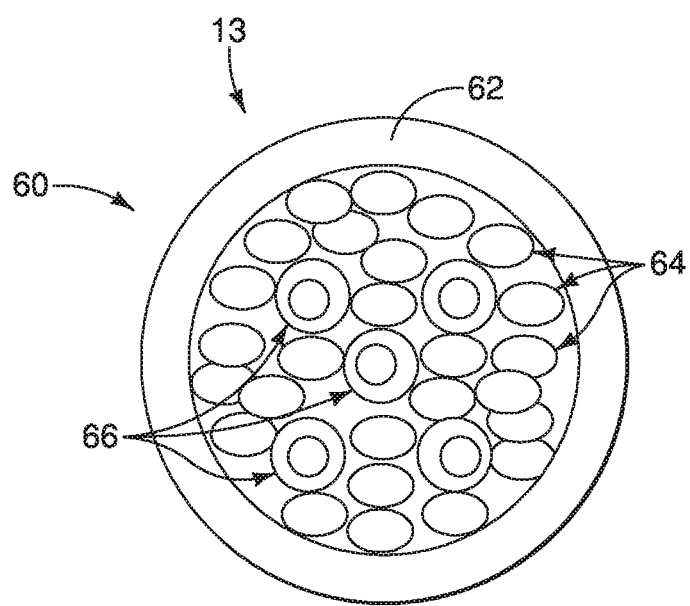
FIG. 12 shows an embodiment of a desiccant assembly.
Figure 13:
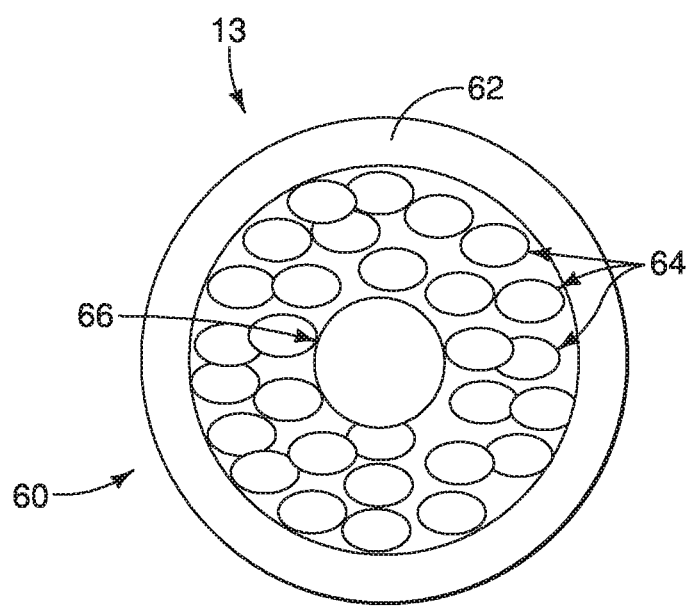
FIG. 13 shows an embodiment of a desiccant assembly.

FIG. 12 shows an exemplary embodiment of a desiccant assembly 60. In some cases, the desiccant assembly is provided as a tube 62 upon which exhaled air flows through. The tube 62 can have an interior filled with a plurality of desiccant beads 64. The desiccant beads 64 can also be arranged such that a plurality of channels 66 are created for exhaled air to flow through. FIG. 13 shows another exemplary embodiment of a desiccant assembly 60. In this embodiment, the tube can have an interior filled with a plurality of desiccant beads 64 arranged such that a single channel 66 is created.

As discussed above, the breath analyzer 10 can include one or more optional gas filters 13. The gas filter(s) 13 help to remove a selected gas (e.g., nitrogen and/or hydrogen) from the exhaled breath. In some embodiments, the gas filter 13 is provided inside of the mouthpiece 12. In other embodiments, the gas filter 13 is provided inside of the chamber 100. Exhaled breath first moves through the gas filter 13 before coming into contact with the sensor 50.

Referring back to FIG. 9, the main body 14 can also include a second compartment configured as an electrical housing 200 that houses various components. In the illustrated embodiment, the electrical housing 200 houses the processor 22, parts of the electrical circuit 24, a power source 28, a display 30, and a wireless connector 32.

During use, a user turns the breath analyzer 10 on by activating the on/off switch 26. The on/off switch 26 can be located anywhere about an exterior surface of the main body 14. This on/off switch 26 in turn prompts the power source 28 to supply voltage to the voltage regulator 34. The voltage regulator 34 regulates and supplies voltage to the at least one gas sensor 50. The resistor 36 also supplies resistance to the at least one gas sensor 50.

A user then blows a breath sample into the first portion 16 of the mouthpiece 12. The breath sample moves past the one way valve 20 and through the optional desiccant/gas filter 60. The breath sample then moves out of the optional desiccant/gas filter 60 and into the chamber 100 where it contacts the at least one gas sensor 50. The breath sample causes a change in resistivity to occur in the at least one gas sensor 50. This change in resistivity is outputted to the processor 22.

The present disclosure also provides a urea breath test ("UBT") method that is an improvement of existing urea breath test methods. This novel UBT uses the breath analyzer 10 described above, which is simple to operate, non-invasive, inexpensive and essentially risk-free. The breath analyzer 10 and related breath test method are available at the point-of-care for self-testing, and the results of the test become available instantaneously.

To undergo this novel UBT, all subjects who wish to be tested for the presence of *H. pylori* infection will need to abstain from taking antibiotics, bismuth, sucralfate, and proton pump inhibitors for two weeks prior to using the breath analyzer 10 and breath test method.

On the day of the breath test method, the subject will follow the following protocol:

In one embodiment the subject will abstain from food and drink intake for one hour prior to breathing into the breath analyzer 10. At the end of the one hour abstinence, the subject will exhale into the mouthpiece 12 for the first time by wrapping his or her lips around the mouthpiece 12 and exhaling breath air into the breath analyzer 10 through the mouthpiece 12 with a prolonged exhalation of approximately 5 seconds of time or over a range of 3-8 seconds of time depending on the age, height and weight of the subject. This provides the baseline exhalation.

After the first exhalation, the subject will ingest urea in quantity calculated as about 5 mg/kg of the subject's body weight or in standard dose of 300 mg or in another standard dose of 125 mg or 250 mg or in another single dose or multiple doses depending on age and weight and general clinical status of the subject. The urea to be ingested can be in two forms. It can be either labeled urea ($^{13}CO\,(NH_2)_2$) or unlabeled urea ($CO\,(NH_2)_2$). Any dose of urea can be taken in a form of a capsule, which can be swallowed with a small amount of water, or can be contained in a small meal, which is either solid (e.g. pudding) or liquid (e.g. citric juice) and that is ingested orally.

In a span of ten to thirty minutes after ingestion of the urea (capsule or urea-containing meal), the subject will exhale for a second time into the device through the mouthpiece 12. The post-urea exhalation through the mouthpiece 12 can be anywhere in a range of from 10 minutes after ingestion up to 30 minutes after ingestion of the urea. For example, the post-urea exhalation can be at 10 minutes after ingestion, at 15 minutes after ingestion, at 20 minutes after ingestion, or at 30 minutes after ingestion of the urea (labeled or unlabeled). In this embodiment, the second exhalation cannot be earlier than 10 minutes after ingestion of the urea (whether in capsule form or as a urea-containing meal), and cannot be later than 100 minutes after ingestion of the urea (whether in capsule form or as a urea-containing meal). Most commonly, the second exhalation will take place at 15-30 minutes after ingestion of the urea or urea containing meal.

In an alternative embodiment, after the baseline exhalation, the subject will ingest a high-protein meal (e.g. hamburger, or high protein bar or equivalent). In a span of 20 to 120 minutes after ingestion of the high-protein meal, the subject will exhale into the mouthpiece 12 for the second time. The second exhalation can be at 20 minutes after ingestion, 30 minutes after ingestion, 50 minutes after ingestion, 80 minutes after ingestion, and 120 minutes after ingestion of the high-protein meal. Most commonly, the second exhalation will take place at 60 minutes after ingestion of the high-protein meal.

The exhaled breaths (baseline and post-urea) enter the main body 14 of the breath analyzer through filter 16 (if present), or directly through the mouthpiece 12 where there is no filter 16. Each breath exits filter 16 (or mouthpiece 12) and enters the one or more gas sensors 50. As the breath samples (baseline exhalation and post-urea exhalation) enter the one or more gas sensors 50 of the breath analyzer 10, the resistivity of the one or more gas sensors 50 changes in relation to the amount of ammonia and/or $CO_2$ and/or $^{13}CO_2$ in the breath under examination.

Where the at least one gas sensor 50 is a single gas sensor, the sensor can detect three gases; ammonia, $CO_2$, and $^{13}CO_2$. Where the at least one gas sensor 50 comprises two gas sensors, one of the gas sensors 50 can detect ammonia, and the other of the gas sensors 50 can detect $CO_2$ and/or $^{13}CO_2$. Where the at least one gas sensor 50 comprises three sensors, one gas sensor 50 can detect ammonia, one gas sensor can detect $CO_2$, and another gas sensor can detect $^{13}CO_2$. Where the at least one gas sensor 50 comprises four gas sensors, one gas sensor 50 can detect ammonia, a different gas sensor can detect $CO_2$, and yet another gas sensor can detect $^{13}CO_2$. Where the at least one gas sensor 50 comprises four gas sensors, one gas sensor can detect ammonia, another gas sensor can detect $CO_2$, yet another gas sensor can detect $^{13}CO_2$, and still yet another sensor can detect humidity.

The change in resistivity due to the presence of ammonia in the breath sample is converted to electrical current and then to parts per billion (ppb) of ammonia. Similarly, the change in resistivity due to the presence of $CO_2$ or $^{13}CO_2$ is converted to electrical current and then to parts per million (ppm). The conversion of delta (post-urea minus baseline) resistivity ($\Delta R$) to ppb and to ppm and any measurement of combinations of the gases will be done with the use of software developed exclusively for the function of the breath analyzer 10 and the electronic circuit 60.

In one embodiment, display 30 will display a numerical value of the concentration of ammonia in ppb and the numerical value of $CO_2$ (and/or $^{13}CO_2$ and/or $^{13}CO_2$:$CO_2$) in ppm. In this embodiment, these numeral values corresponding to the gas concentrations will display through a window on the main body 14 of the breath analyzer 10.

In another embodiment, the numerical value on display 30 will be a single value derived from calculation pertaining to the amount of ammonia plus the amount of $CO_2$ or $^{13}CO_2$ or $^{13}CO_2$:$CO_2$ in the breath of the subject at baseline exhalation and at post-urea exhalation. This calculation can be based on equation for linear predictor of outcome. As an example, the equation can have the form:

(log 10 ammonia×constant for ammonia)+($CO_2$× constant for $CO_2$) or (log 10 ammonia×constant for ammonia)+($^{13}CO_2$× constant for $^{13}CO_2$) or (log 10 ammonia×constant for ammonia)+($CO_2$× constant for $CO_2$)+($^{13}CO_2$×constant for $^{13}CO_2$) or (log 10 ammonia×constant for ammonia)+($^{13}CO_2$: $CO_2$×constant for $^{13}CO_2$:$CO_2$) or another form of polynomial equation where ammonia is in ppb and $^{13}CO_2$ and $CO_2$ are in ppm and $^{13}CO_2$:$CO_2$ is in numerical value.

The constant is derived from analysis (e.g. regression) of multiple values of ammonia, $CO_2$, and $^{13}CO_2$ within the various populations at risk for infection with *H. pylori* and populations in general and within the various dietary habits of such populations and populations in general. The equation will be incorporated into software.

The equation for linear predictor of outcome can have the basic form:

$f(i) = \beta_0 + \beta_1 x_{i1} + \ldots + \beta_p x_{ip}$ for data point $i$.

Below a certain number derived from this equation the subject will be found to be negative for the presence of infection with *H. pylori*. Above a certain number derived from this equation, the subject will be found to be positive for the presence of active infection with *H. pylori*. A small number of inconclusive results will be referred for a repeat of the test and if the results remain inconclusive, the subject will be referred for further evaluation through additional means.

As discussed above, $CO_2$ (or $^{13}CO_2$) and ammonia, which are produced through hydrolysis of urea (unlabeled or labeled) by the *H. pylori*-produced enzyme urease are diffused in the bloodstream through the mucosa and exhaled from the lungs through the exhaled breath. Consumption of urea, either labeled or unlabeled, by an infected subject undergoing testing using this invention will produce elevated amounts of $CO_2$ (or $^{13}CO_2$) and ammonia in the subject's breath.

As also discussed above, the subject undergoing testing using this method will exhale into the breath analyzer 10 twice. The first (baseline) exhalation being after one hour abstinence of food and water, and the second (post-urea) exhalation being after the consumption of urea (labeled or unlabeled) or a high-protein meal or high-protein bar. At all times during the method, the breath analyzer 10 will detect and measure the amount of ammonia, $CO_2$ and/or $^{13}CO_2$.

When ammonia, $CO_2$ and/or $^{13}CO_2$ levels at post-urea exhalation are higher than at baseline, at a level greater than 100% above baseline levels, the subject being tested can be diagnosed as being infected with *H. pylori*. In addition, when the combined ammonia and $CO_2$ (and/or $^{13}CO_2$) levels at post-urea exhalation are at a level greater than 50% above the baseline levels, the subject can be diagnosed as being infected with *H. pylori*.

In diagnosing infection with *H. pylori*, the sensitivity and specificity of the presently disclosed method is higher than with prior methods. This is because the presently disclosed method detects the combined amount of ammonia and $CO_2$ (and/or $^{13}CO_2$), rather than detecting ammonia independently of $CO_2$ (and/or $^{13}CO_2$), or $CO_2$ (and/or $^{13}CO_2$) independently of ammonia. Because the present method measures all products of urea hydrolysis (including ammonia, $^{12}CO_2$, and $^{13}CO_2$), the method of the present disclosure provides the most accurate method for detecting and diagnosing *H. pylori* infection. Simultaneous measurement of $CO_2$ (or $^{13}CO_2$) and ammonia in breath significantly minimizes statistical and other errors which can occur when measuring either $CO_2$ (or $^{13}CO_2$) without ammonia, or ammonia without $CO_2$ (or $^{13}CO_2$).

The combined increase of ammonia and $CO_2$ (and or $^{13}CO_2$) in subjects infected with *H. pylori* subjects is multiplicative (or exponential), not additive. Thus, even small differences between the baseline exhalation and the post-urea exhalation would be diagnostic of *H. pylori* infection hence significantly decreasing false negative results.

The combined increase of ammonia and $CO_2$ (and or $^{13}CO_2$) in infected subjects will be more specific and sensitive for *H. pylori* infection than existing breath test methods because the combination of ammonia and $CO_2$ (and or $^{13}CO_2$) is indicative of, and diagnostic, only for *H. pylori* infection (and no other infection) in individuals without end stage liver disease, encephalopathy, end stage renal disease, and metabolic disease (e.g. Krebs's cycle defect, urea cycle defect).

The following non-limiting examples are intended to show how the breath test method and breath analyzer 10 of the present disclosure can be used to detect *H. pylori* infection in humans, adults and children.

Example 1—Simultaneous Calculation of the Rise of Ammonia and of $CO_2$ in Breath after Ingestion of Unlabeled Urea ($CO(NH_2)_2$ as Diagnostic of *H. pylori* Infection The subject abstains from antibiotics, bismuth, proton pump inhibitors, and sucralfate for two weeks. At the end of the two week period, the subject abstains from food and drink for one hour. At the end of the one hour fast, the subject exhales into the breath analyzer 10 through the mouthpiece 12. The exhalation can last from about 2-10 seconds. In another embodiment, the exhalation continues until a characteristic sound or light coming from the main body 14 indicates that a sufficient amount of exhaled breath has entered the main body 14. By sufficient, it is meant that there is enough of the breath sample to come into contact with the one or more gas sensors 50.

When the baseline exhalation enters the main body 14, the breath sample passes through filter 16 (when it is in place), where gases like NO, $CH_4$, $N_2$, volatile organic compounds, $O_2$, and humidity are blocked from entering the at least one gas sensor 50. Ammonia and $CO_2$ are not blocked by the filter 16 and are allowed to contact the one or more gas sensors 50.

When the breath sample passes to the one or more gas sensors 50, the resistivity of the one or more gas sensors 50 changes according to the amount of ammonia and $CO_2$ present in the exhaled breath. The resistivity of the at least one gas sensor 50 is converted to ppb of ammonia and ppm of $CO_2$ with the use of the electronic circuit 60 and software. The numerical value of ammonia and $CO_2$ obtained during the first exhalation can be stored in memory.

At the end of the baseline exhalation, the subject ingests a known quantity (e.g., 125 mg, 250 mg, or 300 mg, depending on the weight and age of the subject) of unlabeled urea either in tablet or in a small meal or drink. In a span of 10 to 120 minutes post ingestion of unlabeled urea, the subject exhales into the mouthpiece 12 for the second time for the post-urea exhalation, following the same procedure as with the first exhalation. The post-urea exhalation takes place most commonly at 20 minutes post ingestion of unlabeled urea. The post-urea exhalation will not take place earlier than 10 minutes post ingestion, or later than 120 minutes post-urea ingestion of unlabeled urea. The values of ammonia in ppb and of $CO_2$ in ppm of the second exhalation are also stored in memory of the breath analyzer device 10.

The breath analyzer 10 will calculate the final values of ammonia and $CO_2$ as follows:

Final ammonia=post-urea ammonia minus baseline ammonia

Final $CO_2$=post-urea $CO_2$ minus baseline $CO_2$.

Software can be used to convert the resistivity values to final ammonia concentration in ppb and final $CO_2$ concentration in ppm. In subjects who test positive for *H. pylori* infection, the range of values for baseline ammonia would be 20 ppb-200 ppb and the range for post-urea ammonia would be 80 ppb to 600 ppb. Because of the overlap of the baseline and post-urea ammonia values, the actual percent change between baseline and post-urea ammonia will be the marker for the infection with *H. pylori*. When the percent change between baseline and post-urea ammonia is greater than 200%, the subject is considered positive for *H. pylori* infection. When the percent change between baseline and post-urea ammonia is lower than 200%, the subject is negative for *H. pylori* infection.

In subjects who are positive for *H. pylori*, the baseline $CO_2$ concentration is typically below 200 ppm, and the post-urea $CO_2$ concentration is typically above 200 ppm (e.g., ranging from 200-1000 ppm). When the calculated percent change between baseline and post-urea $CO_2$ is greater than 1000%, the subject is considered positive for *H. pylori* infection.

In one embodiment, the positive test result will be the value of percent change of ammonia above 200%, and the value of the percent change of $CO_2$ above 1000%, in a numerical value, in ppb and in ppm respectively, as determined using device specific software.

In another embodiment, the final result, which the device's software will convert into values recognizable by computer program, will be calculated using the equation which takes into account the percent or actual rise of ammonia and the percent or actual rise of $CO_2$ between baseline and post-urea breath samples. The equation can be a logarithmic or statistical equation with the values of two variables (ammonia and $CO_2$) corresponding to the subject being tested, the two constants, and one or more coefficients. The constants and the coefficients are calculated on the basis of demographics and characteristics (e.g. age, gender, race, height and weight) of subjects infected with *H. pylori*.

In another embodiment, the positive *H. pylori* result will be a color (e.g. red), and the negative *H. pylori* result will be a color (e.g. green). In another embodiment, the positive result for *H. pylori* infection will be a plus sign (+) and the negative for *H. pylori* will be a minus sign (−).

The final result can be displayed through a window of the main body 14 of the breath analyzer 10. The final result (whether indicating positive or negative, yes/no, different colored lights, or numerical values of ammonia and of $CO_2$) will be displayed through the window for the main body 14. The breath analyzer 10 will include instructions for the subject undergoing testing so as to allow the subject to interpret the displayed results and provide the subject with recommendations for potential further examination by physician or equivalent personnel and potential treatment options.

Example 2—Simultaneous Calculation of the Rise of Ammonia and of $^{13}CO_2$ in Breath after Ingestion of $^{13}C$ Labeled Urea as Markers for the Presence of *H. pylori* Infection In this example, the subject abstains from antibiotics, bismuth, proton pump inhibitors, and sucralfate for two weeks. At the end of the two-week period, the subject abstains from food and drink for one hour. At the end of the one hour abstinence, the subject exhales into the mouthpiece 10. The exhalation lasts 2-10 seconds or until a characteristic sound or light coming from the main body 14 of the breath analyzer 10 indicates that a sufficient amount of exhaled breath has entered the main body 14 through the mouthpiece 10. By sufficient, it is meant that there is enough of the breath sample to come into contact with the one or more gas sensors 50.

At the end of exhalation and when the sufficient amount of exhaled breath enters from the mouthpiece 10 into the main body 14, it passes first through filter 16 (when present) where gases such as NO, $CH_4$, $N_2$, volatile organic compounds, $O_2$, and humidity are blocked from entering the one or more gas sensors 50. The filter 16 does not block ammonia or $^{13}CO_2$, which gases are allowed to pass through and contact the one or more gas sensors 50.

In another embodiment, as shown in FIG. 3, the exhaled breath enters into the main body 14 from the mouthpiece 10 directly to the one or more gas sensors 50. The resistivity of the one or more gas sensors 50 changes according to the amount of ammonia and $^{13}CO_2$ present in the exhaled breath that comes into contact with the one or more gas sensors 50. The change in resistivity of the one or more gas sensors 50 is converted to ppb of ammonia and to ppm of $^{13}CO_2$ through the use of the electronic circuit 60 and software. The numerical value of ammonia and $^{13}CO_2$ obtained during the first exhalation are stored in the memory of the electronic circuit 60.

At the end of the baseline exhalation, the subject ingests a known quantity (e.g., 125 mg or 250 mg or 300 mg depending on the weight and the age of the subject) of $^{13}C$ labeled urea, either in tablet form or in the form of a small meal or drink. In a span of 10 to 120 minutes post-ingestion of urea, the subject exhales into the mouthpiece 12 for the post-urea exhalation. following the same procedure as with the baseline exhalation. The post-urea exhalation takes place most commonly at 20 minutes post-ingestion of labeled urea. The post-urea exhalation will not take place earlier than 10 minutes post ingestion or later than 120 minutes post ingestion of labeled urea. The concentration values of ammonia in ppb and of $^{13}CO_2$ in ppm are stored in the memory of the device 10.

The device 10 will calculate the final values of ammonia and $^{13}CO_2$ as follows:

Final ammonia=post-urea ammonia minus baseline ammonia

Final $^{13}CO_2$=post-urea $^{13}CO_2$

The designed software will convert the values of final ammonia to ppb and final $^{13}CO_2$ to ppm. In subjects who test positive for *H. pylori* infection, the range of values for baseline ammonia is 20 ppb-200 ppb, and the range for post-urea ammonia is 80 ppb to 600 ppb. Because of the overlap of the baseline and post-urea ammonia values, the percent change between pre-urea and post-urea ammonia will be the marker for the infection with *H. pylori*. When the percent change between pre-urea and post-urea ammonia is greater than 200%, the subject is considered positive for *H. pylori* infection. When the percent change between baseline and post-urea ammonia is lower than 200%, the subject is negative for *H. pylori* infection.

In subjects who are positive for *H. pylori* infection, the baseline $^{13}CO_2$ concentration is typically below 200 ppm, and the post-urea $13CO_2$ concentration is typically above 200 ppm (and can range, e.g., from 200 ppm up to about 1000 ppm).

In one embodiment, the positive test result will be the value of percent change of ammonia above 200% plus the value of the percent change of $13CO_2$ above 1000% as a numerical value determined using device specific software.

In another embodiment, the final result, which the device's software will convert into values recognizable by computer program, will be calculated using an equation which takes into account the percent rise of ammonia and of $13CO_2$ between baseline and post-urea breath samples. The equation can be a logarithmic or statistical equation with the values of two variables (ammonia and $_{13}CO_2$) corresponding to the subject being tested and two constants and one or more coefficients.

In another embodiment, the positive *H. pylori* result will be a color (e.g. red), and the negative *H. pylori* result will be a color (e.g. green). In yet another embodiment, a positive *H. pylori* result will be the plus sign (+) and a negative result for *H. pylori* will be a minus sign (−).

The final result can be displayed through a window on the main body 14 of the device 10. The final result (e.g., indicating positive or negative, yes/no, different colored lights, or numerical values of ammonia and of $13CO_2$) will be displayed through the window on the main body 14. The device 10 will include instructions to allow the subject undergoing testing to interpret the displayed results and provide the subject with recommendations for potential further examination by physician or equivalent personnel and potential treatment options.

Example 3—Calculation of the Rise of the Ratio $^{13}CO_2/^{12}CO_2$, as Delta Over Baseline (DOB), in Human Breath at Baseline and Post-Urea ($^{13}C$ Labeled Urea) and Calculation of Host-Dependent Urea Hydrolysis Rate as Markers for *H. pylori* Infection In this example, the subject abstains from antibiotics, bismuth, proton pump inhibitors, and sucralfate for two weeks. At the end of the two week period, the subject abstains from food and drink for one hour. At the end of the one hour abstinence, the subject exhales into the mouthpiece 12. The baseline exhalation takes place over 2-10 seconds (or longer), or until a characteristic sound or light coming from the main body 14 of the device 10 indicates that a sufficient amount of exhaled breath has entered the main body 14 through the mouthpiece 12. By sufficient, it is meant that there is enough of the breath sample to come into contact with the one or more gas sensors 50. In another embodiment, the subject exhales into the mouthpiece 12 for a short period of time, which can be shorter than 5 seconds and it can be a short burst of exhaled air which enters the device through the mouthpiece 12. In this embodiment, the short burst of exhaled air would be a sufficient amount of breath to enter the device through the mouthpiece 12. There could also be multiple (e.g., more than one) short bursts of exhaled air that will enter the breath analyzer 10 through the mouthpiece 10.

When the sufficient amount of exhaled breath enters the main body 14 of the device 10, and passes through the filter 16, undesirable gases (e.g., $NH_3$, NO, $CH_4$, $N_2$, volatile organic compounds, and/or $0_2$) and humidity are trapped and do not pass through the filter 16. The filter does not block $CO_2$ gas, which gas then comes into contact with the one or more gas sensors 50.

In another embodiment, the device 10 does not contain filter 16, and the sufficient amount of exhaled breath over 2-10 seconds (or bursts of exhaled breath) enters the device 10 through the mouthpiece 12 and reaches the one or more gas sensors 50 directly (i.e., without passing through a filter). In such instances, none of the gases contained in the exhaled breath are blocked when passing from the mouthpiece 10 to the one or more gas sensors 50.

The resistivity of the at least one sensor 50 changes according to the amount of $CO_2$ present in the exhaled breath which comes into contact with the at least one sensor 50. The change in resistivity is converted to ppm of $CO_2$ with the use of the electronic circuit 60 and software. The numerical value in ppm of $CO_2$ obtained during the first exhalation is stored in the memory of the device 10 with the use of software.

In another embodiment, the resistivity of the sensor is not converted to ppm. It remains as a measurement of current that is generated by change in resistivity and is stored in the memory of the device 10 after each exhalation (baseline and post-urea).

At the end of the baseline exhalation, the subject ingests a known quantity (e.g., 125 mg or 250 mg or 300 mg) of $^{13}C$ labeled urea either in capsule or tablet form, or in the form of a small meal or drink. In a span of 10 to 120 minutes post ingestion of $^{13}C$ labeled urea, the subject exhales into the mouthpiece 12 for a second time, following the same procedure as with the baseline exhalation. The post-urea exhalation takes place most commonly at 20 minutes post ingestion of $^{13}C$ labeled urea. The post-urea exhalation will not take place earlier than 10 minutes post ingestion or later than 120 minutes post ingestion of $^{13}C$ labeled urea. After the post-urea exhalation, the values of $CO_2$ in ppm and of $^{13}CO_2$ in ppm are stored in the memory of the device 10.

The device 10 will then calculate the final values of $CO_2$ and $^{13}CO_2$ as follows:

Final $CO_2$=post-urea $CO_2$ minus baseline $CO_2$

Final $^{13}CO_2$=post-urea $^{13}CO_2$ minus baseline $^{13}CO_2$.

In one embodiment the positive test result will be the value of percent change between $^{13}CO_2/CO_2$ of the post-urea exhaled breath over the $^{13}CO_2/CO_2$ of the baseline exhaled breath sample of greater than a certain number which will be called the cut-off point. Above the cut-off point, the result will be positive for the presence of *H. pylori* infection. Below the cut-off point, the result will be negative for *H. pylori* infection. The cut-off point will be calculated during the clinical examination of patients with *H. pylori* infection undergoing the present breath test. The highest level of $^{13}CO_2/CO_2$ demonstrated by the subjects (in clinical trials) who test negative for *H. pylori* infection will be the cut-off point. Levels above this cut-off point will indicate positive for *H. pylori* infection.

In another embodiment, the final result will be calculated using an equation which takes into account the percent rise of $CO_2$ between baseline and post-urea breath samples. The equation can be a logarithmic or statistical equation with the values of one variable ($CO_2$) corresponding to the metabolic rate of the subject being tested, one or more constants, and one or more coefficients. This equation will be used to discern the range of values above which the results will be positive for *H. pylori* infection and below which the results will be negative for *H. pylori* infection.

In another embodiment, the positive *H. pylori* result will be a color (e.g. red), and the negative *H. pylori* result will be a color (e.g. green). In another embodiment, the positive *H. pylori* result will be a plus sign (+) and a negative *H. pylori* result will be the minus sign (−).

The final result will be displayed through a window on the main body 14 of the device 10. The final result (e.g., indicating positive or negative, yes/no, different colored lights, or numerical values of the DOB (Delta over Baseline) for $^{13}CO_2/CO_2$) will be displayed through the window on the main body 12 of the device 10. The device 10 will include instructions to allow the subject undergoing testing to interpret the displayed results and provide the subject with recommendations for potential further examination by physician or equivalent personnel and potential treatment options.

Calculation of host-dependent urea hydrolysis rate (UHR):

$$UHR = CO_2\ produced \times delta\ over\ baseline \times 0.3463,$$
where delta over baseline is defined as the difference between baseline $CO_2$ (or $^{13}CO_2$) and post-urea $CO_2$ (or $^{13}CO_2$).

In certain embodiments, the present disclosure provides a multi-sensor breath analyzer (breathalyzer) device 100 which analyzes the breath of an individual for the presence of gases including, but not limited to, acetaldehyde, 2-propanol, acetonitrile, acrylonitrile, benzene, isoprene, pentane, methylexane, ethane, hydrogen sulfide, triethyl amine, trimethyl amine, carbon disulfide, dimethyl sulfide, 1-Heptene, 1-Octene, 1-Nonene, 1-Decene, methane, ethanol, ammonia ($NH_3$), nitric oxide (NO), nitrogen ($N_2$), hydrogen ($H_2$), Oxygen ($O_2$), carbon dioxide ($CO_2$ or $^{13}CO_2$), carbon monoxide (CO), 2,2,4,6,6-pentamethylheptane, 3,6-dimethyldecane, dodecane, 2,3,4-trimethylhexane, 2,6,8-trimethyldecane, tridecane, undecane, tetradecane, as well as other gases.

Figure 14:
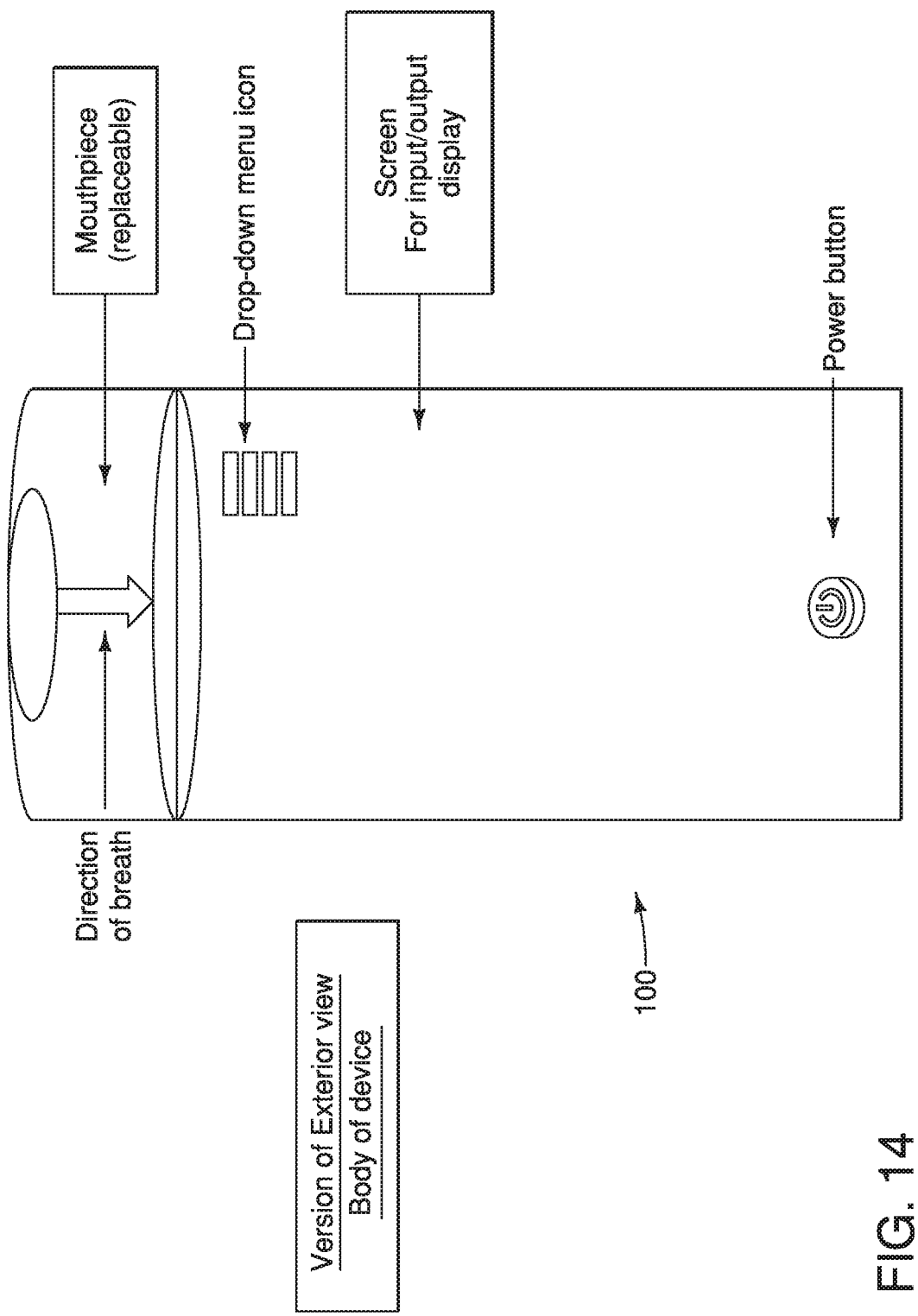
FIG. 14 shows the exterior of a multi-analyte breathalyzer device.

In one embodiment, as shown, for example, in FIG. 14, a breathalyzer device 100 is provided that comprises a main body that can be made of a durable and lightweight material. The main body can include a display (e.g., a touch screen display). The display can extend over (and cover) some or all of one side of the body (e.g., with unbreakable glass). The display can allow for input by the user and for output by the device after the device has finished analyzing the breath of the user.

Figure 15:
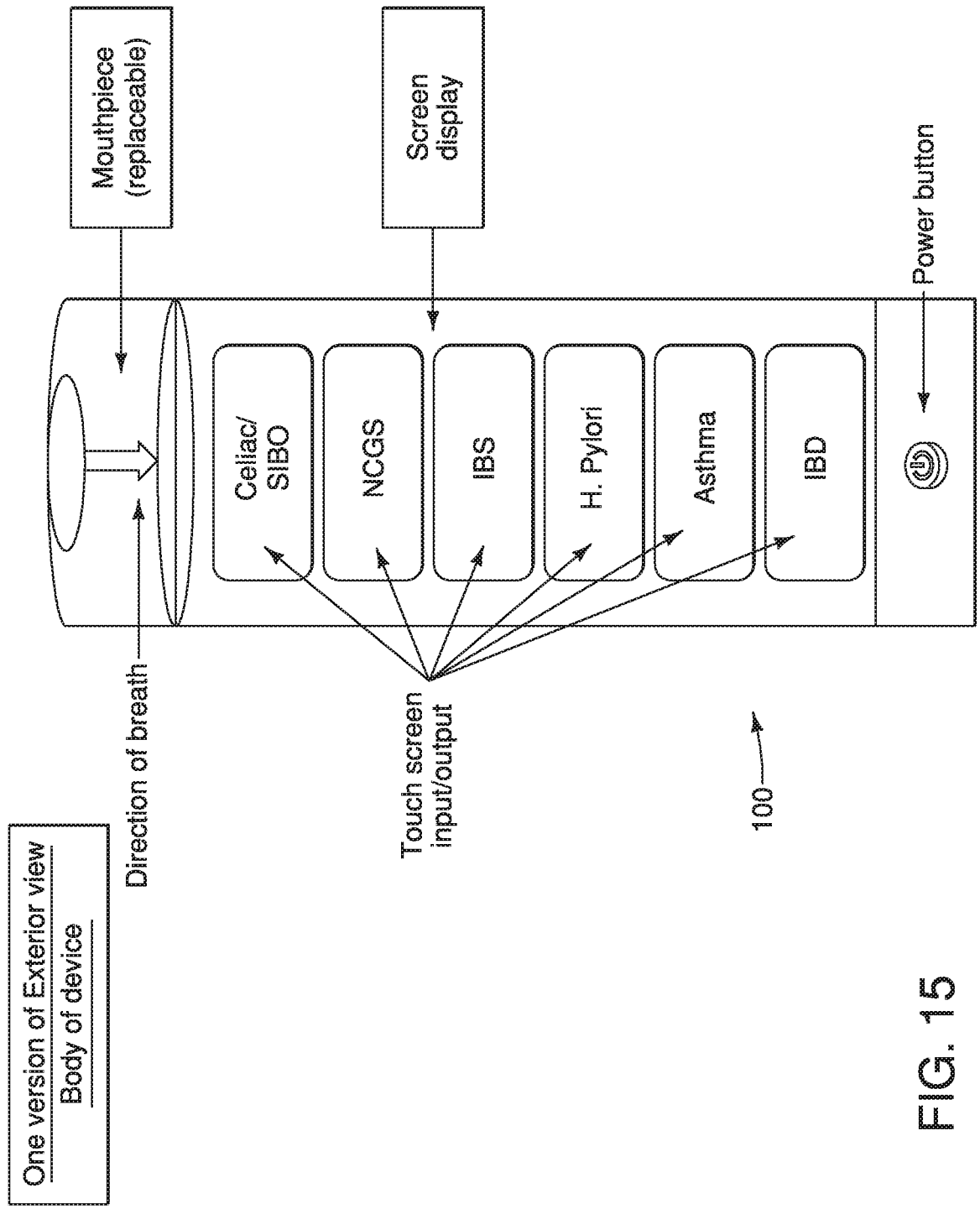
FIG. 15 shows an embodiment of the exterior of a multi-analyte breathalyzer device having an example menu after the menu icon is selected by the user.
Figure 16:
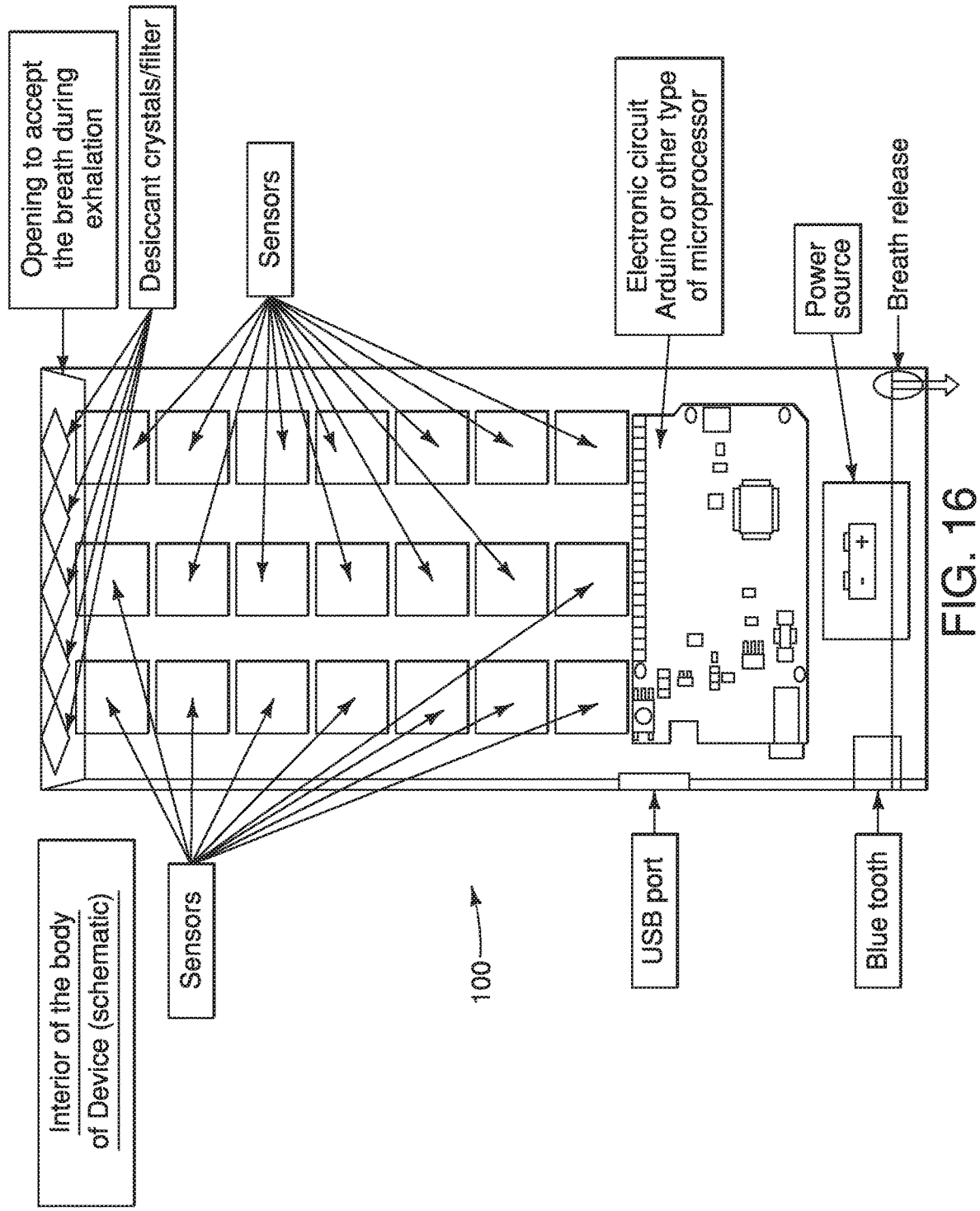
FIG. 16 shows an embodiment of an interior of a multi-analyte breathalyzer device having 21 sensors. The device can contain more sensors as needed. This version of the device has an opening which serves as mouthpiece and accepts the breath sample from the user who applies the mouth around the opening. The opening contains several desiccant crystals embedded in the wall at the opening but the mouth does not come in contact with the crystals. The interior of the device contains an electronic circuit and a microprocessor connected to each sensor, along with Bluetooth, a USB port, a battery and a small hole for release of breath as it exits the device.
Figure 17:
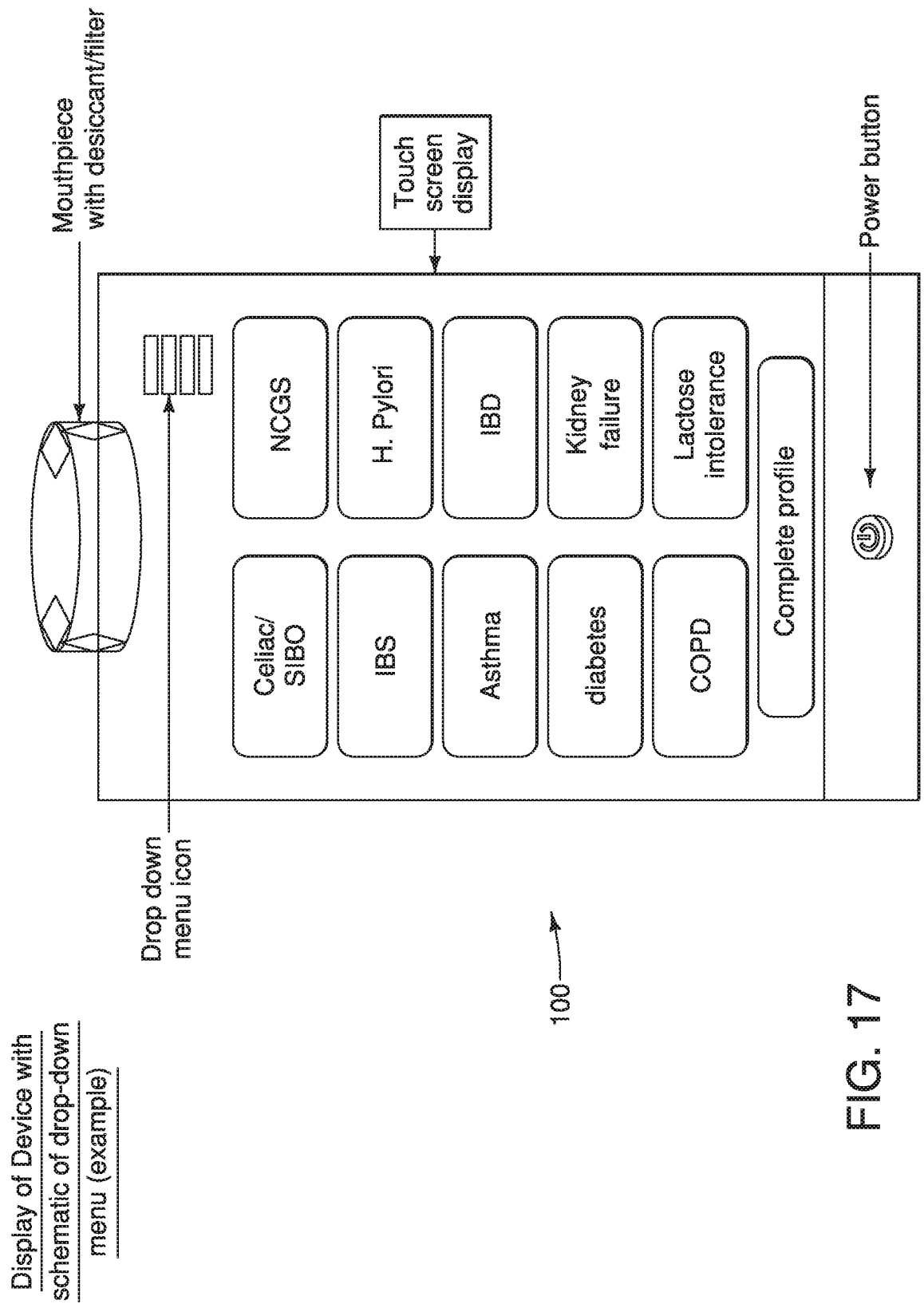
FIG. 17 shows a display of multi-analyte breathalyzer device with an example of the menu after the icon is selected by the user. The user can tap any of the icons which are shown on the display or the icon which says complete profile to receive measurement of all gases which can be measured by the device. A mouthpiece with desiccant and/or filter embedded in the wall of the mouthpiece can be replaceable.
Figure 18:
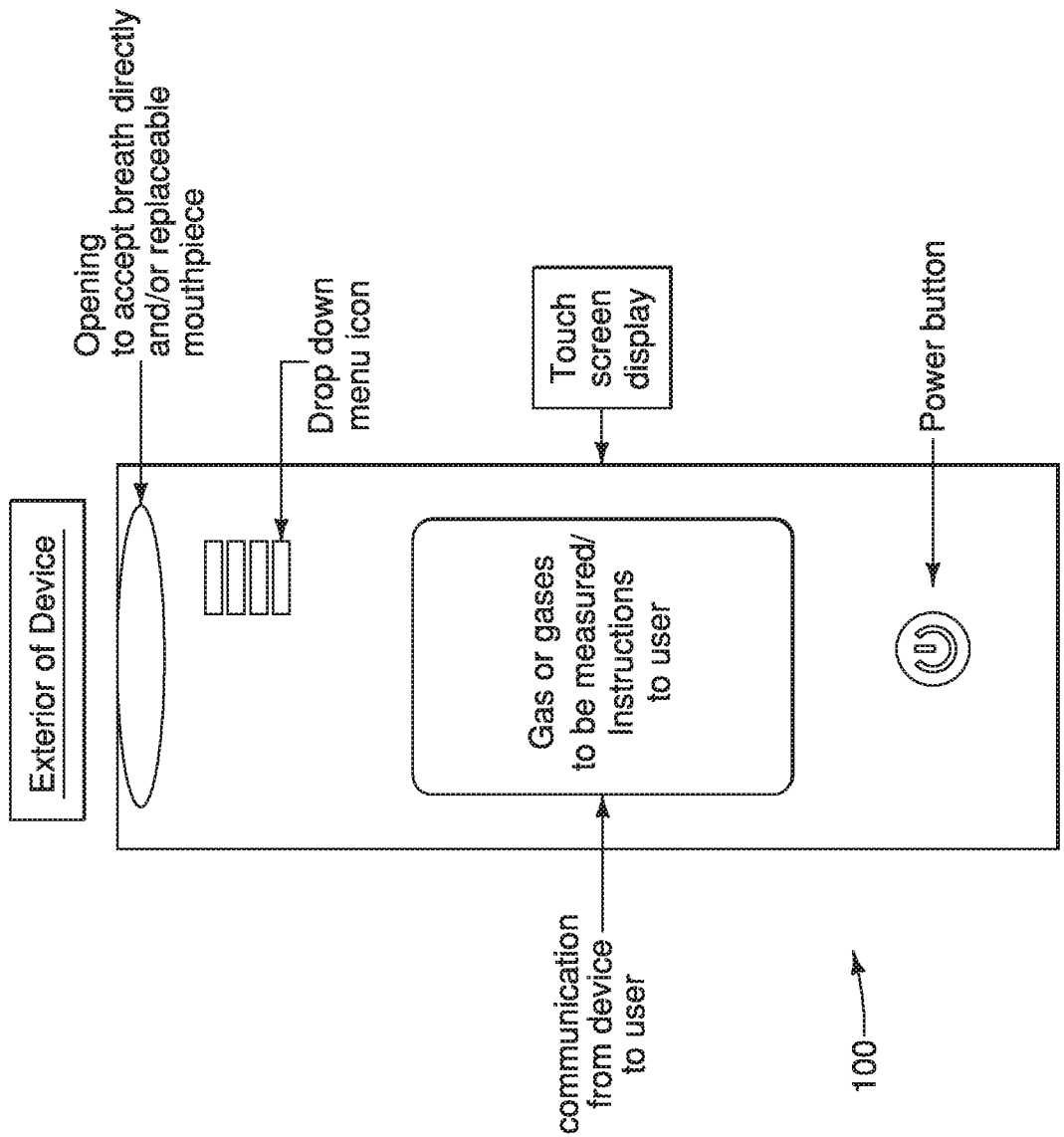
FIG. 18 shows the display of the multi-analyte breathalyzer device after the user selects one of the icons shown in FIGS. 15, 17. The gas or gases to be measured are displayed as are the instructions to the user and proposed follow-up. This version of the device does not contain desiccant/filter inside the mouthpiece. In this version of the device, the desiccant/filter is inside the body of the device in the immediate vicinity of the sensor(s).
Figure 19:
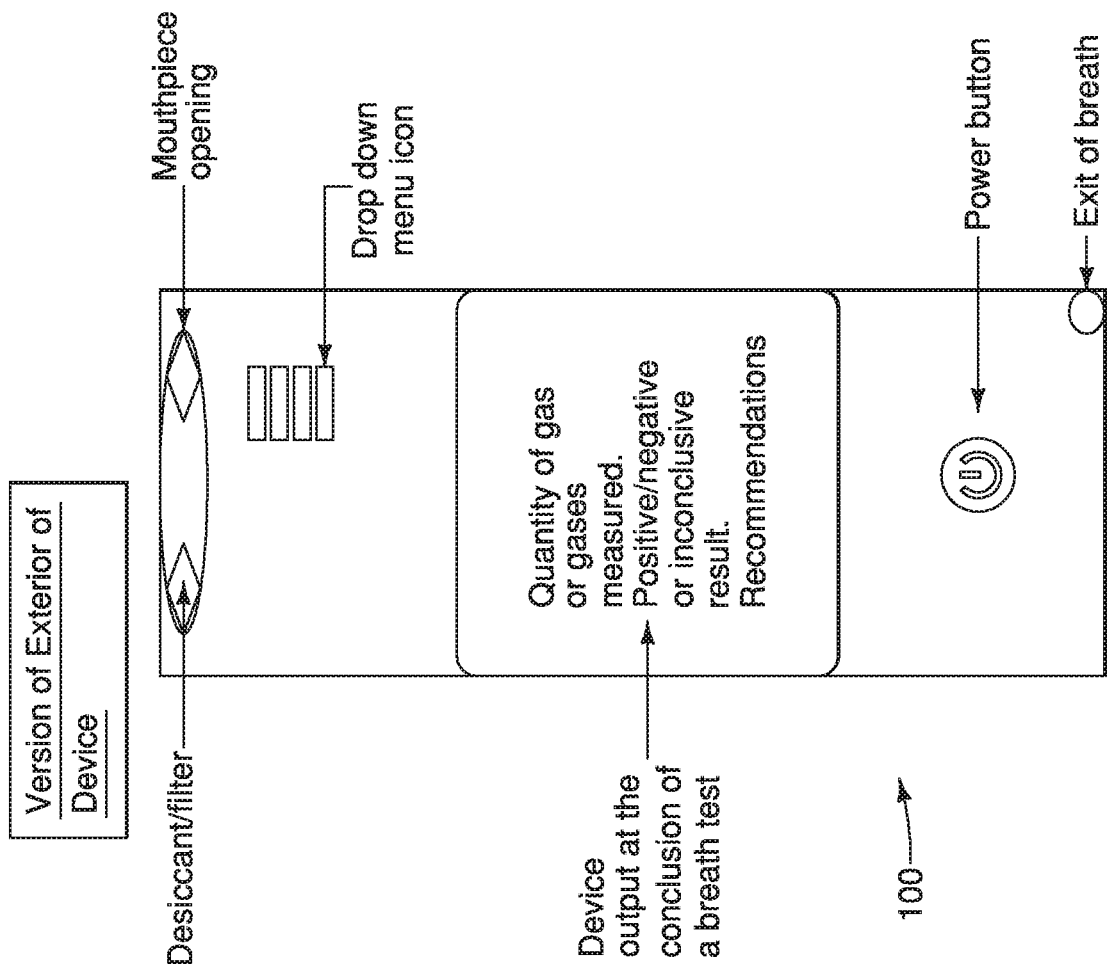
FIG. 19 shows one version of the display of the multi-analyte breathalyzer device after the completion of a breath test. Provided are the results in a form of concentrations of detected gas(es) which were selected to be measured by the device according to the selection by the user from the menu. The device also provides the assessment of the results (normal, below or above normal or inconclusive) based on the selection by the user from the menu and based on the demographics input by the user, and provides recommendations for follow-up.
Figure 20:
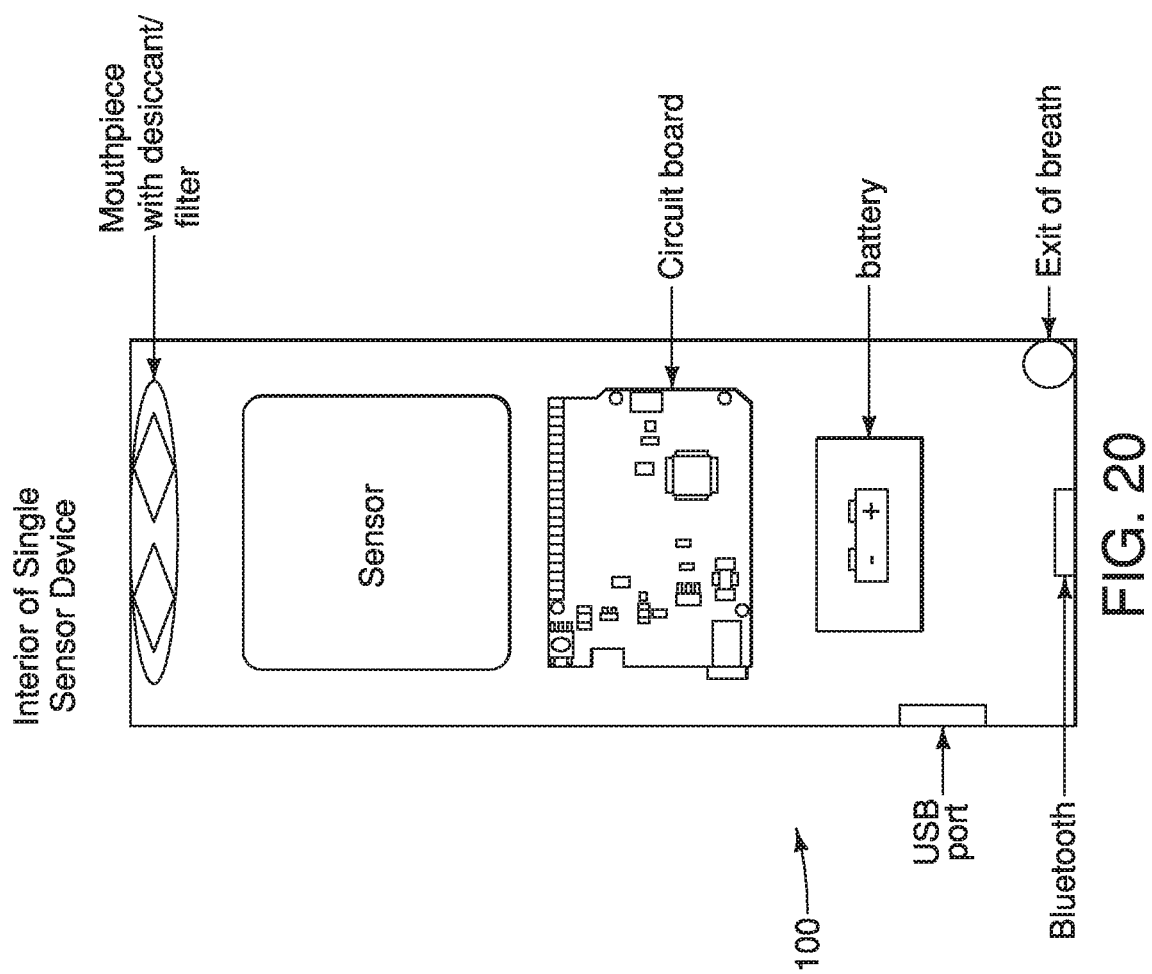
FIG. 20 shows an embodiment of an interior of a single-sensor breath analyzer device. A single sensor is placed inside the device along with electronics and the microprocessor. The device can operate with the use of a battery and can have Bluetooth and a USB port. The device includes an opening for the user to exhale into the device, and desiccant and/or filter are embedded in the wall of the device at the opening.
Figure 21:
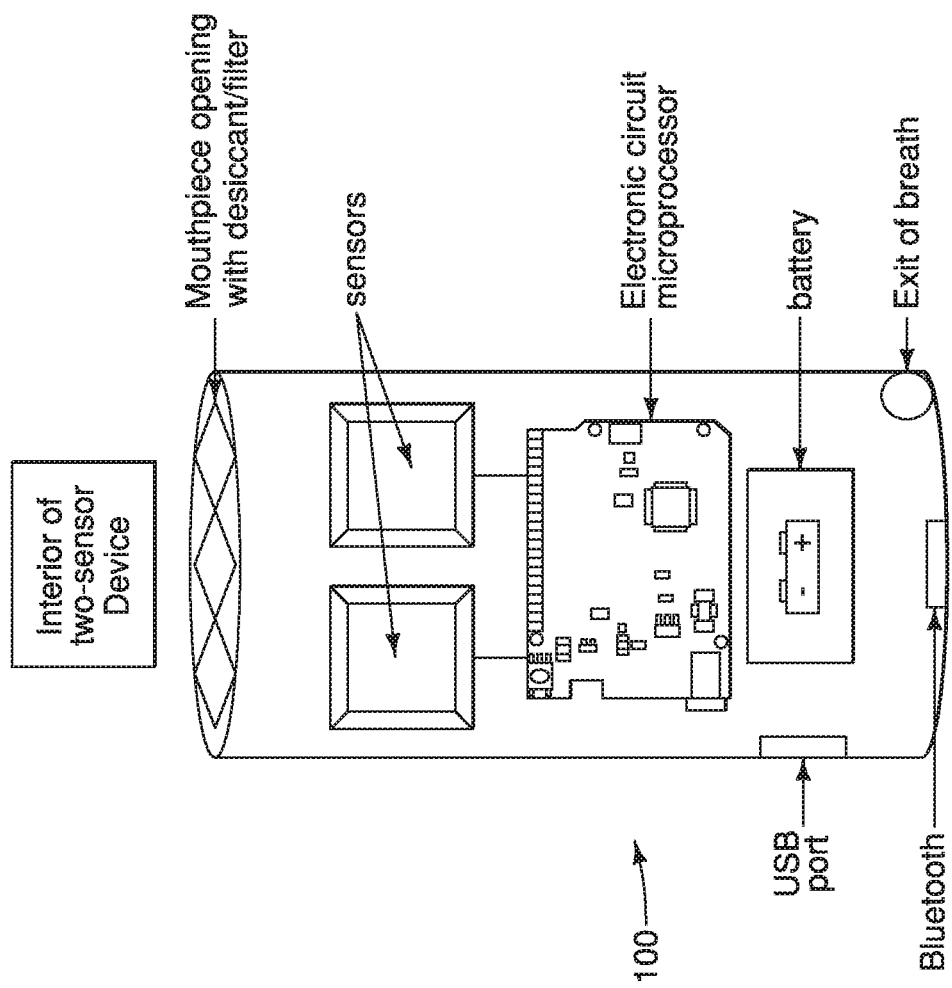
FIG. 21 shows an interior of one version of the multi-analyte breathalyzer device with two sensors. As an example, one sensor can detect ammonia and the other sensor can detect $CO_2$. This version of the device detects both gases from the same breath sample either one time (one breath sample) or multiple times (multiple breath samples), stores the concentration of gas(es) from each measurement and calculates and stores the differences in values between the various measured concentrations according to a predetermined order.
Figure 22:
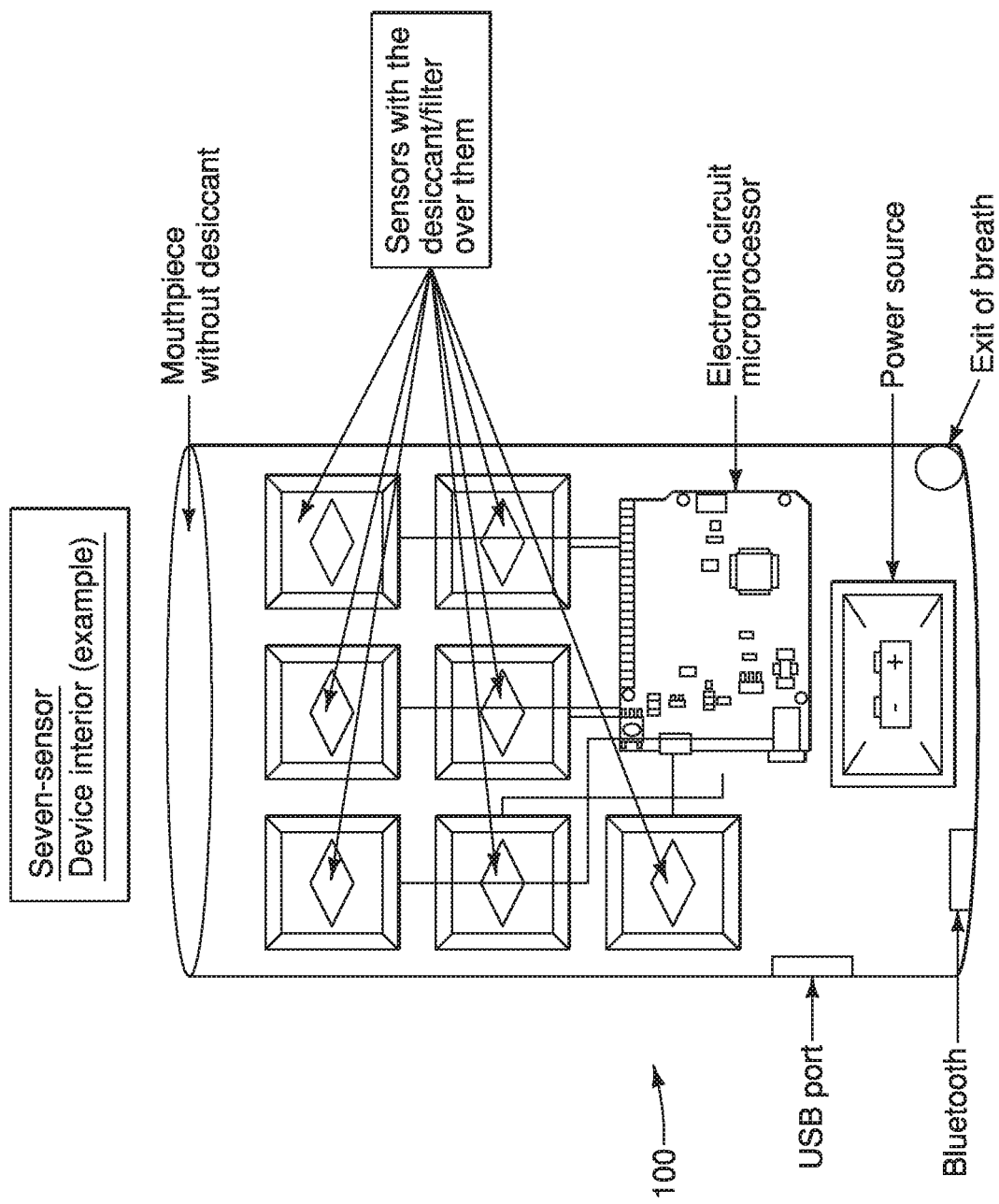
FIG. 22 shows the interior of one version of the multi-analyte breathalyzer device which contains seven sensors. As an example, each sensor can detect each of the following gases: 2-propanol, acrylonitrile, carbon disulfide, dimethyl sulfide, ethanol, isoprene, trimethylamine or any combination of Volatile Organic Compounds (VOCs) which indicate the presence of irritable bowel disease (IBD).

The main body of breathalyzer 100 (FIG. 15) can contain multiple sensors each of which is connected independently to an electronic circuit and microprocessor. The electronic circuit which is connected to each sensor through mechanical connection converts the sensor's resistivity and current to voltage. The microprocessor, which can be Arduino or another type of microprocessor constructed for use by this breathalyzer, analyzes the signal from the sensor and converts it to voltage. Through software, the voltage is converted to units of measurement for each gas to which each sensor is sensitive.

In one embodiment, the sensors of breathalyzer 100 are electrochemical sensors. Electrochemical sensors have a conductive portion and a substrate portion. The conductive portion can include, but is not limited to, gold, platinum, palladium or a mixture of gold and platinum. The substrate portion can include, but is not limited to, doped polymers such as doped polyaniline, doped polypyrrole and others. Polyaniline, when doped with protonic acids such as dinon-aphthalenesulfonic acid (DNNSA), Camphorsulfonic acid (CSA), hydrochloric acid (HCL), sulfosalicylic acid (SSA) and 4-dodecylbenzenesulfonic acid (DBSA), is rendered highly sensitive to gases such as ammonia, hydrogen, nitrogen, methane and hydrogen sulfate. Polypyrrole doped with $FeCl_3$, or with Aminobenzenesulfonic acid (ABSA) or with salicylic acid or another protonic acid is rendered sensitive to $CO_2$ and to $^{13}CO_2$. Electrochemical sensors such as polymer-based sensors (e.g., doped polyaniline and polypyrrole) are more effective and desirable for the breathalyzer 100 because they are stable and operate at room temperature (about 70 degrees Fahrenheit), the temperature at which the present breath analyzer would optimally operate.

In another embodiment the sensors of breathalyzer 100 are metal oxide nanosensors, such as ZnO, PbO-doped $SnO_2$, which are sensitive to hydrogen, methanol, propanol and acetone. Other metal oxides can be used as the sensor material, either independently or in combination with other conductive material placed on metal finger electrodes (e.g., platinum or gold or both) or on floating gate field effect transistors (FGFET) or on carbon nanotubes or on nanowires.

In another embodiment, the sensors of the breathalyzer 100 are polymers (e.g., polyaniline and/or polypyrrole) on conductive materials which are chemical sensitive field effect transistors or floating gate field effect transistors (FGFET) or any other field effect transistors (FETs).

In one embodiment the breathalyzer 100 comprises a removable mouthpiece or an opening on one side of the breathalyzer 100 which is constructed in such manner for the mouth of the user to be wrapped around it. In one embodiment in which the opening of the device serves as mouthpiece, desiccant can be embedded into the wall of the device itself. In another embodiment in which there is a removable mouthpiece, desiccant can be embedded in the wall of the mouthpiece. The desiccant absorbs humidity at the desired level for the operation of the sensors. In addition or alternatively, a filter can be placed in front of some (or all) sensors in order to block gas potentially interfering with a particular sensor which is tasked to detect another gas. Such filter can be in the form of crystal or like silica crystal.

The display of breathalyzer 100, which can be a touch screen display, and which can occupy the entire side of the body of the breathalyzer much like the display of a smart phone, can include a drop down menu which provides the user with several options for testing. Such options can include, but are not limited to, the following medical diagnoses: Celiac Disease, NCGS, SIBO, IBS, diabetes, asthma, COPD, Hyperammonemia, kidney disease, liver disease, lung disease, lactose intolerance, fructose intolerance and others. The user touches one or more than one medical diagnoses and the breathalyzer 100, through its software, asks for input of demographics and characteristics or symptoms compatible with the disease desired to be investigated. After this process is completed to the satisfaction of the preprogrammed algorithm, the user is prompted to exhale into the breathalyzer. The breathalyzer 100 performs the predetermined task of analyzing the breath sample and provides the result with general recommendations.

In one embodiment, the invention provides a breathalyzer device 100 which contains and utilizes 21 or more sensors each of which is sensitive to one gas. These gases can include acetaldehyde, 2-propanol, acetonitrile, acrylonitrile, benzene, isoprene, pentane, methylexane, ethane, hydrogen sulfide, triethyl amine, trimethyl amine, carbon disulfide, dimethyl sulfide, 1-Heptene, 1-Octene, 1-Nonene, 1-Decene, methane, ethanol, ammonia ($NH_3$), nitric oxide (NO), nitrogen ($N_2$), hydrogen ($H_2$), Oxygen ($O_2$), carbon dioxide ($CO_2$ or $^{13}CO_2$), carbon monoxide (CO), 2,2,4,6,6-pentamethylheptane, 3,6-dimethyldecane, dodecane, 2,3,4-trimethylhexane, 2,6,8-trimethyldecane, tridecane, undecane, tetradecane and $H_2O$. Under this embodiment, the breathalyzer 100 can be used for screening and monitoring of celiac disease, non-celiac gluten sensitivity (NCGS), IBD (ulcerative colitis and Crohn's disease), IBS, SIBO, lactose intolerance, fructose intolerance, asthma, COPD, liver disease (steatohepatitis, end stage), *H. pylori* infection, kidney failure and metabolic disease (diabetes, genetic).

In another embodiment, the invention provides a breathalyzer 100 which contains 21 or more sensors and electronically utilizes, on command, all or fewer of the sensors each of which is sensitive to one gas. These gases include but are not limited to acetaldehyde, 2-propanol, acetonitrile, acrylonitrile, benzene, isoprene, pentane, methylexane, ethane, hydrogen sulfide, triethyl amine, trimethyl amine, carbon disulfide, dimethyl sulfide, 1-Heptene, 1-Octene, 1-Nonene, 1-Decene, methane, ethanol, ammonia ($NH_3$), nitric oxide (NO), nitrogen ($N_2$), hydrogen ($H_2$), Oxygen ($O_2$), carbon dioxide ($CO_2$ or $^{13}CO_2$), carbon monoxide (CO), 2,2,4,6,6-pentamethylheptane, 3,6-dimethyldecane, dodecane, 2,3,4-trimethylhexane, 2,6,8-trimethyldecane, tridecane, undecane, tetradecane.

In another embodiment, the invention provides a breathalyzer 100 which contains 21 or more sensors and electronically utilizes, on command, 17 or fewer of the sensors which are sensitive to one gas each. These gases can include, but are not limited to, 2-propanol, acetonitrile, acrylonitrile, benzene, isoprene, pentane, methylexane, ethane, hydrogen sulfide, triethyl amine, trimethyl amine, carbon disulfide, dimethyl sulfide, 1-Heptene, 1-Octene, 1-Nonene, 1-Decene.

In another embodiment, the invention provides a breathalyzer 100 which contains 21 or more sensors and electronically utilizes, on command, 7 or fewer of the sensors which detect one gas each. These gases can include 2-propanol, acrylonitrile, carbon disulfide, dimethylsulfide, ethanol, isoprene, trimethylamine.

In another embodiment, the invention provides a breathalyzer 100 which contains 21 or more sensors and electronically utilizes, on command two or fewer sensors which detect one gas each. Under this embodiment one gas or two gases are detected. These gases include but are not limited to hydrogen ($H_2$), nitric oxide (NO), ammonia, acetone, $CO_2$ or $^{13}CO_2$. Under this embodiment, the diseases for which to screen and monitor include but are not limited to celiac disease, NCGS, IBS, diabetes, *H. pylori* infection, asthma, and kidney failure.

In another embodiment the invention provides a breathalyzer device 100 which contains one or two or more than two sensors each of which is sensitive to either one gas or more than one gas.

In yet another embodiment, the invention provides a breathalyzer device 100 which contains seven or more than seven sensors each of which is sensitive to one gas or more than one gas.

In one embodiment the mouthpiece of the breathalyzer 100 is an opening on one of the side of the breathalyzer device. In another embodiment, the mouthpiece is a separate cylindrical piece which can be removably attached to the device.

In one embodiment, the breathalyzer device 100 contains desiccant (e.g., in the form of crystals) to remove a predetermined amount of humidity from the breath sample and/or a filter to block certain gas or gases from coming into contact with the operating sensors. The crystals are placed either in the interior of the device in the vicinity of the sensor(s) or are placed on or within the wall of the mouthpiece or under the mouthpiece or in the interior of the device.

The following non-limiting examples illustrate certain methods that can be used with breathalyzer 100.

Example 4

The user wishes to examine whether he/she has celiac disease by using the present breathalyzer 100, and can do so using the following procedure:

1. The user presses the power button on the front of the device and the device responds by giving a greeting on the screen and asks the user for information (e.g., name, height, weight, age, gender) and guides him/her to tap the drop-down menu.
2. The user selects (e.g., taps) the drop down menu and finds the celiac/SIBO icon.
3. The user selects (e.g., taps) the celiac/SIBO icon and then the celiac icon.
4. The device responds with a process which the user follows in order to prepare for the test.
A) The preparation which the device gives out states:
B) Abstain from high amount of carbohydrate for 48 hrs. and take nothing by mouth for 8 hrs., overnight, before exhaling once into the device while fasting; and brush your teeth but don't use mouthwash.
5. When the user is ready, he/she turns the device on, selects (e.g., taps) the drop-down menu and selects (e.g., taps) celiac disease.
6. The device asks if the user is ready.
7. The user selects (e.g., taps) yes (or no if not ready).
8. The device asks the user to exhale through the mouthpiece for about 5 seconds and wait.
9. The user exhales for 5 seconds.
10. The device which is programmed through software to test for celiac disease by utilizing the hydrogen sensor blocks all other sensors and operates as a single sensor device.
11. The device returns a quantitative result to the user for the amount of hydrogen in the user's breath sample and offers an assessment of whether the value is within normal limits. The device prompts the user to discuss the finding with his/her healthcare provider.

Example 5

The user wishes to have a full profile of his/her metabolomics, and can do so by performing the following steps. In this case, the breathalyzer device 100 utilizes all sensors simultaneously:
1. The user turns the device on by pressing on the power button.
2. The device gives the greeting and asks the user to select (e.g., tap) the drop-down menu.
3. From the menu, the user selects (e.g., taps) "total profile."
4. The device responds with the following process for the user to follow:
    A) Asks for information and whether the user has used antibiotics or other types of medications.
    B) Depending on the responses, the device will either ask the user to wait for two weeks or would recommend overnight fasting (8 hrs.) and return for the test in the morning.
5. When the user is ready in the morning, he/she has to brush teeth but not use mouthwash.
6. The user turns on the device.
7. The user selects (e.g., taps) the menu.
8. The user selects (e.g., taps) "total profile"
9. The device asks the user to exhale through the mouthpiece for 5 seconds and then wait.
10. The user exhales for 5 seconds.
11. The device utilizes all sensors simultaneously and responds with readout for all detected gases and offers an assessment of whether the values are within normal limits. The device prompts the user to discuss the findings with his/her healthcare provider.

Example 6

The user wishes to examine whether he/she has symptoms compatible with inflammatory bowel disease (IBD), and can do so by performing the following steps:
1. The user turns the breathalyzer device 100 on by pressing on the power button.
2. The device gives a greeting and asks the user to select (e.g., tap) the drop-down menu.
3. From the menu the user selects IBD.
4. The device responds with the following process:
    A) Asks for information and whether the user has used antibiotics or any other medications which treat IBD;
    B) Depending on the answer, the device responds with the process.
5. The user returns after overnight fast (8 hrs.) in the morning after brushing teeth but not using mouthwash.
6. The user turns the device on.
7. The user selects (e.g., taps) the menu.
8. The user selects (e.g., taps) IBD.
9. The device asks if the user is ready.
10. The user responds yes.
11. The device asks the user to exhale for 5 seconds and wait.
12. The user exhales for 5 seconds.
13. The device blocks all sensors except those which are programmed by the software to operate under the IBD request.
14. The device responds with the measurement of each of these gases and an assessment of whether they are within normal limits. The device prompts the user to discuss the findings with his/her healthcare provider.

Example 7

The user suffers from asthma with an inflammatory component and is required to monitor the efficacy of the treatment and wishes to prevent flare-ups of the disease. In this case, the user seeks to measure nitric oxide in his/her breath, and can do so by performing the following steps:
1. The user turns on the breathalyzer device 100 by pressing on the power button.
2. The device provides a greeting and asks the user to select (e.g., tap) the drop-down menu icon.
3. On the menu, the user selects (e.g., taps) asthma/Nitric Oxide.
4. The device returns with instructions as to how to proceed with the breath test, in this case to breathe for about 5-10 seconds into the device through its mouth piece or opening and asks the user if he or she is ready.
5. The user selects (e.g., taps) yes.
6. The device asks for input of data such as name, age, gender, height and weight.
7. After the input, the device blocks all sensors except for the one which detects nitric oxide.
8. The device measures the nitric oxide in the user's breath sample.
9. The device stores the result and compares it to previous results from the same user.
10. The device outputs the result on the screen and gives the trendline from the previous results from tests of the past 1-365 days and provides an assessment indicating whether the results are within normal limits or not.
11. The device prompts the user to discuss the findings with his/her health care provider.

While some preferred embodiments of the invention have been described, it should be understood that various changes, adaptations and modifications may be made therein without departing from the spirit of the invention and the scope of the appended claims.

EMBODIMENTS

1. A hand-held, point-of-care universal platform for breath testing device for the concurrent or separate detection of one or more than one gases and volatile organic compounds contained in human breath in adults and children for screening, diagnosis and monitoring of diseases of the gastrointestinal tract, the liver, the lungs and the kidneys and diseases of metabolism and infections.
    a. Wherein the breath testing device of embodiment 1 is used to screen and monitor multiple ailments including but not limited to 1) inflammatory bowel diseases (e.g. Crohn's disease and Ulcerative colitis); 2) genetic, immunological and allergy induced (e.g. asthma, celiac disease, gluten allergy, non-celiac gluten sensitivity); 3) intestinal malabsorption (e.g. lactose intolerance, fructose intolerance, short bowel syndrome, small intestinal bacterial overgrowth); 4) infections (e.g. *Helicobacter pylori*, parasitic infections, viral or bacterial intestinal infections); 5) malignancies (e.g. lung cancer, lymphoma, breast cancer, stomach cancer); and 6) organ failure such as liver, kidney and heart failure.
    b. Wherein the breath testing device in embodiment 1 is an electrochemical universal platform device and contains one or more than one nanosensors sensitive to one gas or more than one gas and to one or more than one volatile organic compounds contained in human breath.
   i. Wherein one or more than one nanosensor is sensitive to oxygen ($O_2$), nitrogen ($N_2$), hydrogen ($H_2$), methane ($CH_4$), ammonia ($NH_3$), $CO_2$, $^{13}CO_2$, Nitric Oxide (NO) and to Volatile Organic Compounds (VOCs) including but not limited to ammonia ($NH_3$), acetone, methanol, ethanol and methane ($CH_4$), acetaldehyde, 2-propanol, acetonitrile, acrylonitrile, benzene, isoprene, pentane, methylexane, ethane, hydrogen sulfide, triethyl amine, trimethylamine, carbon disulfide, dimethyl sulfide, 1-Heptene, 1-Octene, 1-Nonene, 1-Decene, octane, nonene, dodecane, cyclohexane, 2-butane, indole, ester, carbon disulfide, pentane, nitric oxide (NO), ethane and propane.
   ii. Wherein one or more than one nanosensors are thermoelectric sensors, electrochemical sensors, or conducting polymers film or thin film or thick film, or metal oxide.
   iii. Wherein one or more than one sensors are FTIR-based sensors or electroluminescence-based sensors.
   iv. Wherein one or more than one sensors are sensors made of conductive material such as polyaniline and polypyrrole modified with the use of compounds such as graphene, hydrochloric acid (HCL), Camphorsulfonic acid (CSA), salicylic acid, DNNSA, Aminobenzenesulfonic acid (ABSA), metal oxides either independently or in combination with other conductive material placed on metal finger electrodes (platinum or gold or both) or on floating gate field effect transistors (FGFET) or on carbon nanotubes or on nanowires.
   v. Wherein types of conductive materials are chemical sensitive field effect transistors or floating gate field effect transistors (FGFET) or any other field effect transistors (FETs).
   vi. Wherein one or more than one nanosensors operate at room temperature, at approximately 70 degrees Fahrenheit.
   vii. Wherein one or more than one nanosensors operate when heated above 70 degrees Fahrenheit.
  c. Wherein the breath testing device in embodiment 1 is directed through its software to utilize one or more than one sensors to perform one breath test or more than one breath tests and allows for input of data which is stored and returns an output at the end of each breath test.
   i. Wherein an individual's input directs the device to utilize one or more than one sensors at a time to perform one or more than one breath tests at a time
   ii. Wherein the input is in the form of directions through software which serve the device in embodiment 1.
   iii. Wherein the input is applied through the touch screen of the device in embodiment 1.
   iv. Wherein the output is remotely sent to a computer or a smart phone
2. A hand-held, point-of-care universal breath testing platform device which contains multiple sensors, each of those sensors sensitive to one gas or to more than one gas such as hydrogen ($H_2$), methane ($CH_4$), ammonia ($NH_3$), carbon dioxide ($CO_2$), $^{13}$carbon dioxide ($^{13}CO_2$), oxygen ($O_2$), nitrogen ($N_2$), nitric oxide (NO), acetaldehyde, ethanol, 2-propanol, acetonitrile, acrylonitrile, benzene, isoprene, pentane, methylexane, ethane, hydrogen sulfide, triethyl amine, trimethyl amine, carbon disulfide, dimethyl sulfide, 1-Heptene, 1-Octene, 1-Nonene, 1-Decene.
  a. Wherein one or more than one sensor is sensitive to volatile organic compounds and gases contained in human breath of healthy or non-healthy child or adult.
3. Wherein the exhaled breath enters the universal breath testing platform device of embodiment 1 through a mouthpiece or through an opening or through a port or through a valve on the body of the device with the use of a bag.
  a. Wherein the mouthpiece is removable and is removably attached to the body of the device, is replaced every time the same device is used by more than one individual.
  b. Wherein the mouthpiece is non-removable and is non-removably attached to the body of the device, is used by one and the same individual one or more than one time.
  c. Wherein the opening on the body of the device accepts the exhaled breath directly from the mouth of the person exhaling breath.
  d. Wherein the port is part of the body of the device and accepts the exhaled breath through an external source like a bag or a canister or any other structure capable to contain breath sample and to attach to the body of the device through a port or a valve or through a port and a valve.
  e. Wherein the valve is attached on the device through an opening and can accept a bag in which breath is exhaled and stored until the time the bag can be introduced into the device by emptying the bag into the device through the opening and the valve on the body of the device.
4. Wherein each sensor in the universal breath testing platform device of embodiment 1 is isolated from the other sensors
  a. Wherein each sensor is isolated from the other sensors and is located in its own physical space within the body of the device
  b. Wherein each sensor is isolated electronically form the other sensors and is electronically attached to the microprocessor
  c. Wherein every isolated sensor is connected electronically to the same microprocessor as the remaining sensors
  d. Wherein, while the exhaled breath reaches all sensors, the microprocessor analyzes the signal from only the sensor which is electronically permitted by the software of the device in embodiment 1 to analyze.
  e. Wherein the microprocessor concurrently analyzes and reports on the screen display of the device in embodiment 1 all analyzed gases in units of measurement.
5. Wherein the signal from one or more than one nanosensors which comes in contact with the exhaled breath generates current which in turn is converted to voltage with the use of convertor. The voltage is converted to the concentration of one or more than one gas with the use of processor and is displayed on the device in quantitative or in numerical value or in qualitative (Positive/Negative) or visual signal or in color.

a. Wherein the concentration of one or more than one gasses is displayed on the body of the device through an LED screen either in quantitative or numerical value or in qualitative (Positive/Negative) or visual signal in color (e.g. red for negative/green for positive).
6. A method of use of the device in embodiment 1 for the diagnosis of celiac disease.
7. A method of use of the device in embodiment 1 for the diagnosis of *Helicobacter pylori* infection.
8. A method of use of the device in embodiment 1 for the diagnosis of Hyperammonemia
    a. Wherein the device in embodiment 1 detects ammonia in breath at a level above a certain level.
    b. Wherein the level of ammonia is above 1 ppm.
9. A method of use of the device in embodiment 1 for the diagnosis of end stage liver disease.
10. A method of use of the device in embodiment 1 for the diagnosis of lung inflammation and disease.
11. A method of use for the device of embodiment 1 for the analysis of breath metabolome
    a. Wherein the breath metabolome is characteristic of a pattern of bacteria present in the large bowel of healthy individuals
    b. Wherein the breath metabolome is characteristic of a pattern of bacteria present in the large bowel of non-healthy individuals

What is claimed is:

1. A breath test method, comprising the steps of:
(a) providing a portable breath analyzer, the portable breath analyzer comprising:
    (i) a removable mouthpiece; and
    (ii) a main body, the main body comprising:
        a first sensor including an ammonia selective material and a first electrically-conductive material, the first sensor having a first resistivity, wherein the first sensor is configured such that the first resistivity changes in the first sensor when the first sensor detects ammonia;
        a second sensor including a carbon dioxide selective material and a second electrically-conductive material, the second sensor having a second resistivity,
        wherein the second sensor is configured such that the second resistivity changes in the second sensor when the second sensor detects carbon dioxide;
        a processor; and
        an electrical circuit, wherein the first and second electrically-conductive materials are operably connected by the electrical circuit to the processor, wherein the first and second sensors are configured to output respective one of the first and second resistivities to the processor, and wherein the processor is configured to receive the first and second resistivities and determine a concentration of ammonia and carbon dioxide detected by respective one of the first and second sensors;
(b) receiving, by the portable breath analyzer, a baseline breath sample exhaled by a subject into the removable mouthpiece;
(c) measuring, by the processor, the first resistivity of the first sensor that occurs when the baseline breath sample contacts the first sensor;
(d) prompting the subject to ingest labeled urea ($^{13}CO(NH_2)_2$) or unlabeled urea ($CO(NH_2)_2$);
(e) receiving, by the portable breath analyzer, a post-urea breath sample exhaled by the subject into the removable mouthpiece;
(f) measuring, by the processor, the first resistivity of the first sensor that occurs when the post-urea breath sample contacts the first sensor; and
(g) comparing, by the processor, the measured first resistivity of the baseline breath sample to the measured first resistivity of the post-urea breath sample.

2. The breath test method of claim 1 further comprising resetting or replacing the first sensor and the second sensor before the step of receiving a post-urea breath sample into the removable mouthpiece.

3. A breath analyzer comprising:
a removable mouthpiece; and
a main body, the main body comprising:
    a first sensor including an ammonia selective material and a first electrically-conductive material, the first sensor having a first resistivity, wherein the first sensor is configured such that the first resistivity in the first sensor changes when the first sensor has a contact with ammonia;
    a second sensor including a carbon dioxide selective material and a second electrically-conductive material, the second sensor having a second resistivity, wherein the second sensor is configured such that the second resistivity in the second sensor changes when the second sensor has a contact with carbon dioxide;
    a processor; and
    an electrical circuit, wherein the first and second electrically-conductive materials are operably connected by the electrical circuit to the processor, wherein the first and second sensors are configured to output voltage and respective one of the first and second resistivities to the processor, and wherein the processor is configured to receive the first and second resistivities and determine a concentration of ammonia and carbon dioxide detected by respective one of the first and second sensors.

4. The breath analyzer of claim 3, wherein the breath analyzer is a portable electrochemical device, and wherein the first or second sensor comprises at least one nanosensor sensitive to one or more gas or volatile organic compound contained in human breath.

5. The breath analyzer of claim 4, wherein the at least one nanosensor is sensitive to oxygen ($O_2$), nitrogen ($N_2$), hydrogen ($H_2$), methane ($CH_4$), ammonia ($NH_3$), $CO_2$, $^{13}CO_2$, Nitric Oxide (NO) and Volatile Organic Compounds (VOCs).

6. The breath analyzer of claim 3, wherein the first or second sensor comprises at least one nanosensor, the at least one nanosensor comprising a thermoelectric sensor, an electrochemical sensor, or a conducting polymer film, thin film, thick film, or metal oxide.

7. The breath analyzer of claim 3, wherein the first or second sensor comprises an FTIR-based sensor or an electroluminescence-based sensor.

8. The breath analyzer of claim 3, wherein the first sensor comprises polyaniline in contact with the first electrically-conductive material, wherein the polyaniline comprises polyaniline doped with a dopant that increases pH sensitivity of the polyaniline, and wherein the polyaniline has a resistivity that increases in response to increased presence of ammonia.

* * * * *